(12) United States Patent
Kelly et al.

(10) Patent No.: US 6,638,972 B2
(45) Date of Patent: Oct. 28, 2003

(54) CHROMAN AND BENZOFURAN DERIVATIVES AS 5-HYDROXYTRYPTAMINE-6 LIGANDS

(75) Inventors: Michael Gerard Kelly, Thosand Oaks, CA (US); Lynne Padilla Greenblatt, Lambertville, NJ (US); Gan Zhang, Niwot, CO (US); Yvette L. Palmer, Yardley, PA (US); Steven Edward Lenicek, Plainsboro, NJ (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 10/263,913

(22) Filed: Oct. 3, 2002

(65) Prior Publication Data

US 2003/0153599 A1 Aug. 14, 2003

Related U.S. Application Data

(60) Provisional application No. 60/326,970, filed on Oct. 4, 2001.

(51) Int. Cl.[7] ..................... A61K 31/352; C07D 311/04
(52) U.S. Cl. ................. 514/456; 549/407; 549/467; 548/217; 548/454; 546/196; 546/282.7; 544/151; 544/359; 514/469; 514/375; 514/337; 514/320; 514/253; 514/233.5
(58) Field of Search ................. 514/456, 469, 514/233.5, 253, 320, 337, 375; 549/407, 467; 544/151, 359; 546/196, 282.7; 548/217, 454

(56) References Cited

U.S. PATENT DOCUMENTS

| 3,915,963 A | * | 10/1975 | Hirose et al. ................ 514/469 |
| 5,134,140 A | * | 7/1992 | Stack ......................... 514/212 |
| 5,541,199 A | | 7/1996 | Mewshaw |
| 5,670,667 A | | 9/1997 | Mewshaw |
| 5,684,039 A | * | 11/1997 | Mewshaw ................... 514/456 |
| 5,767,132 A | | 6/1998 | Bottcher et al. |
| 5,824,682 A | | 10/1998 | Van Lommen et al. |
| 5,962,513 A | | 10/1999 | Schohe-Loop et al. |

FOREIGN PATENT DOCUMENTS

WO    WO 00/76990 A1    12/2000

OTHER PUBLICATIONS

Mewshaw, R. E.; et al, Journal of Medicinal Chemistry, 1997, 40, 4235–4256.

* cited by examiner

Primary Examiner—Charanjit S. Aulakh
(74) Attorney, Agent, or Firm—Barbara L. Lences

(57) ABSTRACT

The present invention provides a compound of formula I and the use thereof for the therapeutic treatment of disorders relating to or affected by the 5-HT6 receptor.

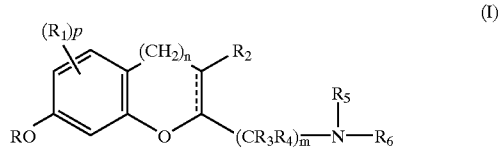

20 Claims, No Drawings

CHROMAN AND BENZOFURAN DERIVATIVES AS 5-HYDROXYTRYPTAMINE-6 LIGANDS

This application claims priority from provisional application Serial No. 60/326970, filed on Oct. 4, 2001, the entire disclosure of which is hereby incorporated by reference.

BACKGROUND OF THE INVENTION

Various central nervous system disorders such as anxiety, depression, motor disorders, etc., are believed to involve a disturbance of the neurotransmitter 5-hydroxytryptamine (5-HT) or serotonin. Serotonin is localized in the central and peripheral nervous systems and is known to affect many types of conditions including psychiatric disorders, motor activity, feeding behavior, sexual activity, and neuroendocrine regulation among others. The effects of serotonin are regulated by the various 5-HT receptor subtypes. Known 5-HT receptors include the 5-HT1 family (e.g. 5-HT1A), the 5-HT2 family (e.g. 5-HT2A), 5-HT3, 5-HT4, 5-HT5, 5-HT6 and 5-HT7 subtypes.

The recently identified human 5-hydroxytryptamine-6 (5-HT6) receptor subtype has been cloned, and the extensive distribution of its mRNA has been reported. Highest levels of 5-HT6 receptor mRNA have been observed in the olfactory tubercle, the striatum, nucleus accumbens, dentate gyrus and CA1, CA2 and CA3 regions of the hippocampus. Lower levels of 5-HT6 receptor mRNA are seen in the granular layer of the cerebellum, several diencephalic nuclei, amygdala and in the cortex. Northern blots have revealed that 5-HT6 receptor mRNA appears to be exclusively present in the brain, with little evidence for its presence in peripheral tissues. The high affinity of a number of antipsychotic agents for the 5-HT6 receptor, in addition to its mRNA localization in striatum, olfactory tubercle and nucleus accumbens suggests that some of the clinical actions of these compounds may be mediated through this receptor. Therefore, 5-HT6 receptor ligands are believed to be of potential use in the treatment of certain CNS disorders such as anxiety, depression, epilepsy, obsessive compulsive disorders, attention deficit disorder, migraine, cognitive memory enhancement (e.g. for the treatment of Alzheimer's disease), sleep disorders, feeding disorders (e.g. anorexia and bulimia), panic attacks, withdrawal from drug abuse (e.g. cocaine, ethanol, nicotine and benzodiazepines), schizophrenia, or the like; or in the treatment of certain gastrointestinal disorders such as irritable bowel syndrome.

Therefore, it is an object of this invention to provide compounds which are useful as therapeutic agents in the treatment of a variety of central nervous system disorders related to or affected by the 5-HT6 receptor.

It is another object of this invention to provide therapeutic methods and pharmaceutical compositions useful for the treatment of central nervous system disorders related to or affected by the 5-HT6 receptor.

It is a feature of this invention that the compounds provided may also be used to further study and elucidate the 5-HT6 receptor.

These and other objects and features of the invention will become more apparent by the detailed description set forth hereinbelow.

SUMMARY OF THE INVENTION

The present invention provides a chroman or benzofuran compound of formula I

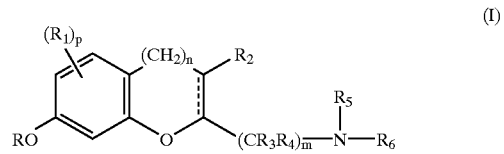

wherein
R is a $C_1$–$C_6$alkyl, aryl or heteroaryl group each optionally substituted;

$R_1$ is halogen, CN, $OR_7$, $CO_2R_8$, $CONR_9R_{10}$, $SO_xR_{11}$ or a $C_1$–$C_6$alkyl, $C_2$–$C_6$alkenyl, $C_2$–$C_6$alkynyl, $C_3$–$C_6$cycloalkyl, cycloheteroalkyl, phenyl or heteroaryl group each optionally substituted;

$R_2$, $R_3$ and $R_4$ are each independently H or an optionally substituted $C_1$–$C_6$ alkyl group with the proviso that when R is an optionally substituted $C_1$–$C_6$alkyl group then $R_2$, $R_3$ and $R_4$ must be H;

$R_5$ and $R_6$ are each independently H or a $C_1$–$C_6$alkyl, $C_3$–$C_6$cycloalkyl or heterocyclylalkyl group each optionally substituted or $R_3$ and $R_4$ may be taken together with the atom to which they are attached to represent a 3- to 10-membered optionally substituted mono- or bicyclic ring system optionally containing one or two additional heteroatoms selected from N, O or S with the proviso that when R is an optionally substituted $C_1$–$C_6$alkyl group then $R_5$ and $R_6$ must be other than a $C_3$–$C_6$cycloalkyl or cycloheteroalkyl group;

m is an integer of 1, 2, 3 or 4;

n is 0 or 1;

p is 0 or an integer of 1, 2 or 3;

=== represents a single bond or a double bond;

x is 0 or an integer of 1 or 2;

$R_7$ is H, $CO_2R_{12}$ or a $C_1$–$C_6$alkyl, $C_2$–$C_6$alkenyl, $C_2$–$C_6$alkynyl, aryl or heteroaryl group each optionally substituted;

$R_8$ and $R_{12}$ are each independently H or a $C_1$–$C_6$alkyl, $C_2$–$C_6$alkenyl, $C_2$–$C_6$alkynyl, $C_3$–$C_6$cycloalkyl, cycloheteroalkyl, aryl or heteroaryl group each optionally substituted;

$R_9$ and $R_{10}$ are each independently H or an optionally substituted $C_1$–$C_6$alkyl group; and $R_{11}$ is a $C_1$–$C_6$alkyl, aryl or heteroaryl group each optionally substituted; or the stereoisomers thereof or a pharmaceutically acceptable salt thereof.

The present invention also provides methods and compositions useful for the therapeutic treatment of central nervous system disorders related to or affected by the 5-HT6 receptor.

DETAILED DESCRIPTION OF THE INVENTION

The 5-hydroxytryptamine-6 (5-HT6) receptor is one of the most recent receptors to be identified by molecular cloning. Its ability to bind a wide range of therapeutic compounds used in psychiatry, coupled with its intriguing distribution in the brain has stimulated significant interest in new compounds which are capable of interacting with or affecting said receptor. Significant efforts are being made to understand the possible role of the 5-HT6 receptor in psychiatry, cognitive dysfunction, motor function and control, memory, mood and the like. To that end, compounds which demonstrate a binding affinity for the 5-HT6 receptor are earnestly sought both as an aid in the study of the 5-HT6 receptor and as potential therapeutic agents in the treatment of central nervous system disorders, for example see C. Reavill and D. C. Rogers, Current Opinion in Investigational Drugs, 2001, 2(1):104–109, Pharma Press Ltd.

Surprisingly, it has now been found that chroman and benzofuran derivatives of formula I demonstrate 5-HT6 affinity. Advantageously, said chroman and benzofuran derivatives may be used as effective therapeutic agents for the treatment of central nervous system (CNS) disorders associated with or affected by the 5-HT6 receptor. Accordingly, the present invention provides chroman and benzofuran derivatives of formula I

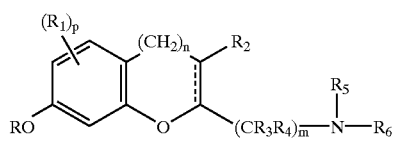

(I)

wherein

R is a $C_1$–$C_6$alkyl, aryl or heteroaryl group each optionally substituted;

$R_1$ is halogen, CN, $OR_7$, $CO_2R_8$, $CONR_9R_{10}$, $SO_xR_{11}$ or a $C_1$–$C_6$alkyl, $C_2$–$C_6$alkenyl, $C_2$–$C_6$alkynyl, $C_3$–$C_6$cycloalkyl, cycloheteroalkyl, phenyl or heteroaryl group each optionally substituted;

$R_2$, $R_3$ and $R_4$ are each independently H or an optionally substituted $C_1$–$C_6$ alkyl group with the proviso that when R is an optionally substituted $C_1$–$C_6$alkyl group then $R_2$, $R_3$ and $R_4$ must be H;

$R_5$ and $R_6$ are each independently H or a $C_1$–$C_6$alkyl, $C_3$–$C_6$cycloalkyl or heterocyclylalkyl group each optionally substituted or $R_3$ and $R_4$ may be taken together with the atom to which they are attached to represent a 3- to 10-membered optionally substituted mono- or bicyclic ring system optionally containing one or two additional heteroatoms selected from N, O or S with the proviso that when R is an optionally substituted $C_1$–$C_6$alkyl group then $R_5$ and $R_6$ must be other than a $C_3$–$C_6$cycloalkyl or cycloheteroalkyl group;

m is an integer of 1, 2, 3 or 4;

n is 0 or 1;

p is 0 or an integer of 1, 2 or 3;

===  represents a single bond or a double bond;

x is 0 or an integer of 1 or 2;

$R_7$ is H, $CO_2R_{12}$ or a $C_1$–$C_6$alkyl, $C_2$–$C_6$alkenyl, $C_2$–$C_6$alkynyl, aryl or heteroaryl group each optionally substituted;

$R_8$ and $R_{12}$ are each independently H or a $C_1$–$C_6$alkyl, $C_2$–$C_6$alkenyl, $C_2$–$C_6$alkynyl, $C_3$–$C_6$cycloalkyl, cycloheteroalkyl, aryl or heteroaryl group each optionally substituted;

$R_9$ and $R_{10}$ are each independently H or an optionally substituted $C_1$–$C_6$alkyl group; and $R_{11}$ is a $C_1$–$C_6$alkyl, aryl or heteroaryl group each optionally substituted; or the stereoisomers thereof or a pharmaceutically acceptable salt thereof.

As used in the specification and claims, the term halogen designates Br, Cl, I or F and the term cycloheteroalkyl designates a $C_5$–$C_7$cycloalkyl ring system containing 1 or 2 heteroatoms, which may be the same or different, selected from N, O or S and optionally containing one double bond. Exemplary of the cycloheteroalkyl ring systems included in the term as designated herein are the following rings wherein X is NR, O or S.

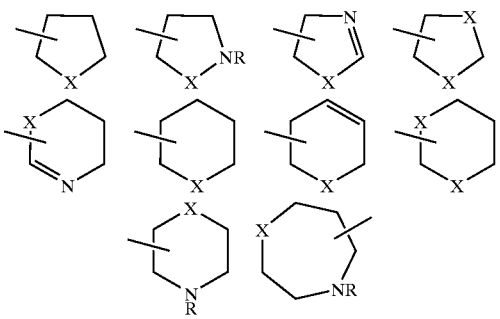

Similarly, as used in the specification and claims, the term heteroaryl designates a $C_5$–$C_{10}$ aromatic ring system containing 1 or 2 heteroatoms, which may be the same or different, selected from N, O or S. Such heteroaryl ring systems include pyrrolyl, azolyl, oxazolyl, thiazolyl, imidazolyl, furyl, thienyl, quinolinyl, isoquinolinyl, indolinyl, benzothienyl, benzofuranyl, benzisoxazolyl or the like. The term haloalkyl as used herein designates a $C_nH_{2n+1}$ group having from one to 2n+1 halogen atoms which may be the same or different and the term haloalkoxy as used herein designates an $OC_nH_{2n+1}$ group having from one to 2n+1 halogen atoms which may be the same or different.

In the specification and claims, when the terms $C_1$–$C_6$alkyl, $C_2$–$C_6$alkenyl, $C_2$–$C_6$alkynyl, $C_3$–$C_7$cycloalkyl, cycloheteroalkyl, phenyl or heteroaryl are designated as being optionally substituted, the substituent groups which are optionally present may be one or more of those customarily employed in the development of pharmaceutical compounds or the modification of such compounds to influence their structure/activity, persistence, absorption, stability or other beneficial property. Specific examples of such substituents include halogen atoms, nitro, cyano, thiocyanato, cyanato, isocyanato, hydroxyl, alkyl, haloalkyl, alkoxy, haloalkoxy, amino, alkylamino, dialkylamino, formyl, alkoxycarbonyl, carboxyl, alkanoyl, alkylthio, alkylsuphinyl, alkylsulphonyl, carbamoyl, alkylamido, phenyl, phenoxy, benzyl, benzyloxy, heterocyclyl or cycloalkyl groups, preferably halogen atoms or lower alkyl groups. Typically, 0–3 substituents may be present. When any of the foregoing substituents represents or contains an alkyl substituent group, this may be linear or branched and may contain up to 12, preferably up to 6, more preferably up to 4 carbon atoms.

Pharmaceutically acceptable salts may be any acid addition salt formed by a compound of formula I and a pharmaceutically acceptable acid such as phosphoric, sulfuric, hydrochloric, hydrobromic, citric, maleic, malonic, mandelic, succinic, fumaric, acetic, lactic, nitric, sulfonic, p-toluene sulfonic, methane sulfonic acid or the like.

Compounds of the invention include esters, carbamates or other conventional prodrug forms, which in general, are functional derivatives of the compounds of the invention and which are readily converted to the inventive active moiety in vivo. Correspondingly, the method of the invention embraces the treatment of the various conditions described hereinabove with a compound of formula I or with a compound which is not specifically disclosed but which, upon administration, converts to a compound of formula I in vivo. Also included are metabolites of the compounds of the present invention defined as active species produced upon introduction of these compounds into a biological system.

Compounds of the invention may exist as one or more stereoisomers. The various stereoisomers include enantiomers, diastereomers, atropisomers and geometric isomers. One skilled in the art will appreciate that one stereoisomer may be more active or may exhibit beneficial effects when enriched relative to the other stereoisomer(s) or when separated from the other stereoisomer(s). Additionally, the skilled artisan knows how to separate, enrich or selectively prepare said stereoisomers. Accordingly, the present invention comprises compounds of Formula I, the stereoisomers thereof and the pharmaceutically acceptable salts thereof. The compounds of the invention may be present as a mixture of stereoisomers, individual stereoisomers, or as an optically active form.

Preferred compounds of the invention are those compounds of formula I wherein R is an optionally substituted $C_1$–$C_6$alkyl group. Also preferred are those compounds of formula I wherein n is 1 and === represents a single bond. Another group of preferred compounds of formula I are those compounds wherein m is 1.

More preferred compounds of the invention are those compounds of formula I wherein R is an optionally substituted $C_1$–$C_6$alkyl group and $R_5$ and $R_6$ are each independently H or an optionally substituted $C_1$–$C_6$alkyl group. Another group of more preferred compounds of the invention are those compounds wherein n is 1; m is 1; p is 0 or 1; === represents a single bond; R is a $C_1$–$C_4$alkyl group optionally substituted with phenyl; and $R_2$ is H. Further, more preferred compounds of the invention are those compounds of formula I wherein m is 1; p is 0 or 1; R is benzyl; $R_2$ is H; and $R_5$ and $R_6$ are each independently H or $C_1$–$C_6$alkyl optionally substituted with hydroxy.

Among the preferred compounds of the invention are:

[3-(benzoxazol-6-yloxy)-propyl]-(7-benzyloxy-chroman-2-ylmethyl)amine; (7-benzyloxy-chroman-2-ylmethyl)-(3-methoxy-propyl)amine;
3-{[(2S)-7-benzyloxy-chroman-2-ylmethyl]-amino}-propan-1-ol;
3-{[(2R)-7-benzyloxy-chroman-2-ylmethyl]-amino}-propan-1-ol;
(7-benzyloxy-chroman-2-ylmethyl)-butyl-amine;
2-[(7-benzyloxy-chroman-2-ylmethyl)-amino]-ethanol;
(7-benzyloxy-chroman-2-ylmethyl)-(3-benzyloxy-propyl)-amine;
(7-benzyloxy-chroman-2-ylmethyl)-(3-phenyl-propyl)-amine;
(7-benzyloxy-chroman-2-ylmethyl)-(3-butoxy-propyl)-amine;
benzyl-(7-benzyloxy-chroman-2-ylmethyl)-amine;
3-{[7-(naphthalen-2-ylmethoxy)-chroman-2-ylmethyl]-amino}-propan-1-ol;
3-{[7-(4-nitro-benzyloxy)-chroman-2-ylmethyl]-amino}-propan-1-ol;
3-{[7-(2-chloro-benzyloxy)-chroman-2-ylmethyl]-amino}-propan-1-ol;
3-[(7-cyclohexylmethoxy-chroman-2-ylmethyl)-amino]-propan-1-ol;
3-{[7-(3-methoxy-benzyloxy)-chroman-2-ylmethyl]-amino}-propan-1-ol;
3-[(7-phenoxy-chroman-2-ylmethyl)-amino]-propan-1-ol;
(7-benzyloxy-chroman-2-yl)-methylamine;
2-[(7-benzyloxy-chroman-2-ylmethyl)-amino]-ethanol;
3-[(6-benzyloxy-benzofuran-2-ylmethyl)-amino]-propan-1-ol;
benzyl-(6-benzyloxy-benzofuran-2-ylmethyl)-amine;
3-[(7-benzyloxy-chroman-2-ylmethyl)-methyl-amino]-propan-1-ol;
(6-benzyloxy-2,3-dihydro-benzofuran-2-yl)-methylamine;
2-[(6-benzyloxy-2,3-dihydro-benzofuran-2-ylmethyl)-amino]-ethanol;
3-[(6-benzyloxy-2,3-dihydro-benzofuran-2-ylmethyl)-amino]-propan-1-ol;
[(2R)-7-benzyloxy-chroman-2-ylmethyl]-(3-methoxy-propyl)-amine;
[(2R)-7-benzyloxy-chroman-2-ylmethyl]-(3-ethoxy-propyl)-amine;
4-[(2R)-7-benzyloxy-chroman-2-ylmethyl]-morpholine;
benzyl-((2R)-7-benzyloxy-chroman-2-ylmethyl)-amine;
[(2R)-7-benzyloxy-chroman-2-ylmethyl]-(3-butoxy-propyl)-amine;
[(2R)-7-benzyloxy-chroman-2-ylmethyl]-tert-butyl-amine;
[(2R)-7-benzyloxy-chroman-2-ylmethyl]-(3-phenoxy-propyl)-amine;
3-[(7-benzyloxy-6-chloro-chroman-2-ylmethyl)-amino]-propan-1-ol;
1-(7-benzyloxy-chroman-2-ylmethyl)-4-(2-methoxy-phenyl)-piperazine;
7-{3-[(7-benzyloxy-6-chloro-chroman-2-ylmethyl)-amino]-propoxy}-chromen-2-one;
3-[(7-phenethyloxy-chroman-2-ylmethyl)-amino]-propan-1-ol;
3-{[7-(thiophen-3-ylmethoxy)-chroman-2-ylmethyl]-amino}-propan-1-ol;
(7-benzyloxy-chroman-2-ylmethyl)-[2-(1H-indol-3-yl)-ethyl]-amine;
3-[(7-benzyloxy-3-methyl-chroman-2-ylmethyl)-amino]-propan-1-ol;
3-{[7-(2-methyl-thiazol-4-ylmethoxy)-chroman-2-ylmethyl]-amino}-propan-1-ol;
7-{3-[(7-benzyloxy-chroman-2-ylmethyl)-amino]-propoxy}-chromen-2-one;
1-(7-benzyloxy-chroman-2-ylmethyl)-4-(2-methoxy-phenyl)-1,2,3,6-tetrahydropyridine;
3-[1-(7-benzyloxy-chroman-2-ylmethyl)-piperidin-4-yl]-1H-indole;
(7-benzyloxy-chroman-2-ylmethyl)-[3-(4-nitro-phenoxy)-propyl]-amine;
3-[(7-benzyloxy-3-butyl-chroman-2-ylmethyl)-amino)-propan-1-ol;
(7-benzyloxy-chroman-2-ylmethyl)-[3-(3-chloro-phenoxy)-propyl]-amine;
(7-benzyloxy-chroman-2-ylmethyl)-[3-(4-chloro-phenoxy)-propyl]-amine;
(7-benzyloxy-chroman-2-ylmethyl)-[3-(3-nitro-phenoxy)-propyl]-amine;
(7-benzyloxy-chroman-2-ylmethyl)-(2-benzylsulfanyl-ethyl)-amine;
(2R)-2-[(7-benzyloxy-chroman-2-ylmethyl)-amino]-3-benzylsulfanyl-propan-1-ol;

the stereoisomers thereof; or the pharmaceutically acceptable salts thereof.

Compounds of the invention may be prepared using conventional synthetic methods and, if required, standard separation and isolation techniques. For example, compounds of formula I wherein m is 1; n is 1; ═══ represents a single bond; and $R_2$ is H (Ia) may be prepared by reacting a 2',4'-dihydroxyacetophenone derivative of formula III with diethyl oxalate in the presence of a base to form the 7-hydroxy-4-oxo-benzopyran-2-carboxylate of formula IV; reducing said formula IV compound via catalytic hydrogenation to give the corresponding 7-hydroxychroman-2-carboxylate of formula V; O-alkylating said formula V compound with an appropriate alkyl halide in the presence of a base to give the 7-alkoxychroman of formula VI; reducing said formula VI compound with lithium aluminum hydride to give the alcohol of formula VII; treating said formula VII alcohol with carbon tetrabromide in the presence of triphenylphosphine to give the alkyl bromide of formula VIII and reacting said formula VIII compound with an amine, $HNR_5R_6$, to give the desired product of formula Ia. The reaction sequence is illustrated in flow diagram I wherein X is Cl or Br.

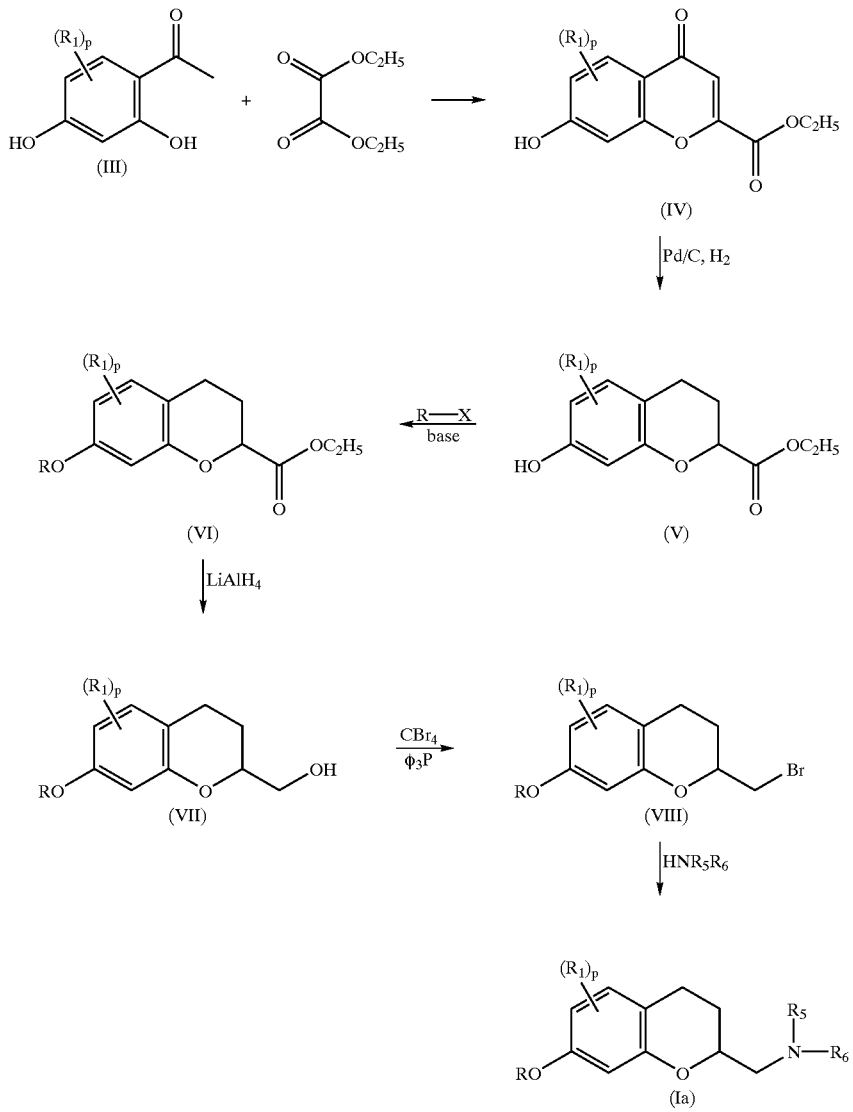

Individual stereoisomers of compounds of formula Ia may be obtained via the resolution of a compound of formula V using a conventional resolving agent such as chirazyme L-6 to give the enantiomerically pure R-ester and S-acid isomers and carrying said isomers through the reaction sequence shown hereinabove in flow diagram I to give the desired R and S stereoisomers of the compound of formula Ia. The reaction is shown in flow diagram II.

Flow Diagram II

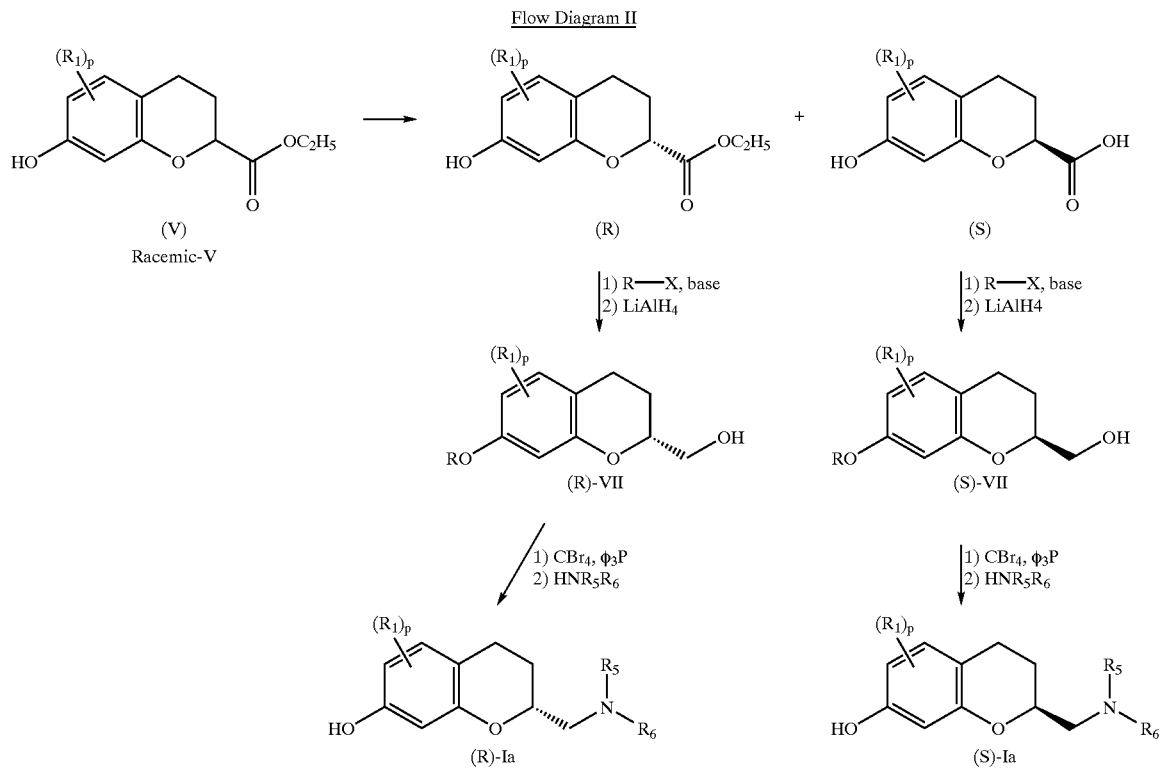

Compounds of formula I wherein m is 1; n is 0; and ≡ represents a single bond (Ib) may be prepared by selectively alkylating a 2,4-dihydroxybenzaldehyde derivative of formula IX to give the corresponding alkoxy compound of formula X; converting said formula X compound to a benzofuran ester of formula XI with methyl bromoacetate and potassium carbonate and subsequent cyclization with magnesium methoxide; hydrolyzing said formula XI ester to the corresponding carboxylic acid of formula XII; reducing said formula XII compound using sodium amalgam to give the corresponding dihydrobenzofuran of formula XIII; coupling said formula XIII compound with an amine, $HNR_5R_6$ to form the amide of formula XIV; and reducing said formula XIV amide to give the desired product of formula Ib. The reaction sequence is shown in flow diagram III wherein X is Cl or Br.

Flow Diagram III

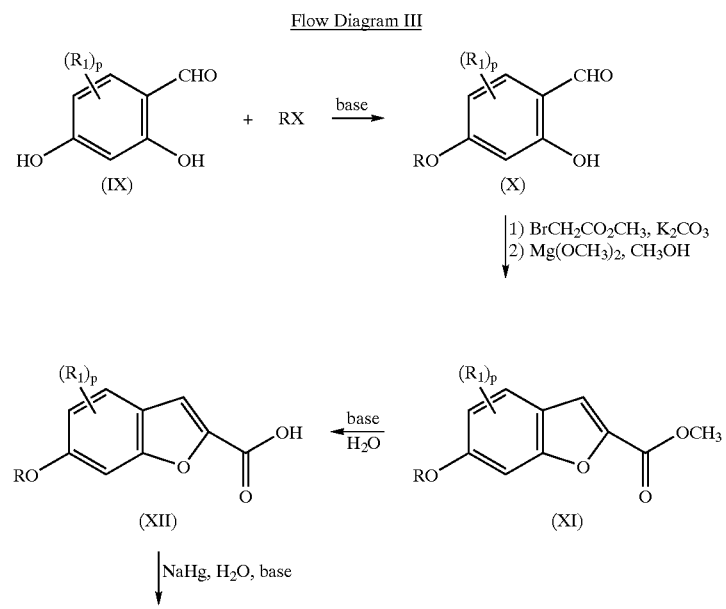

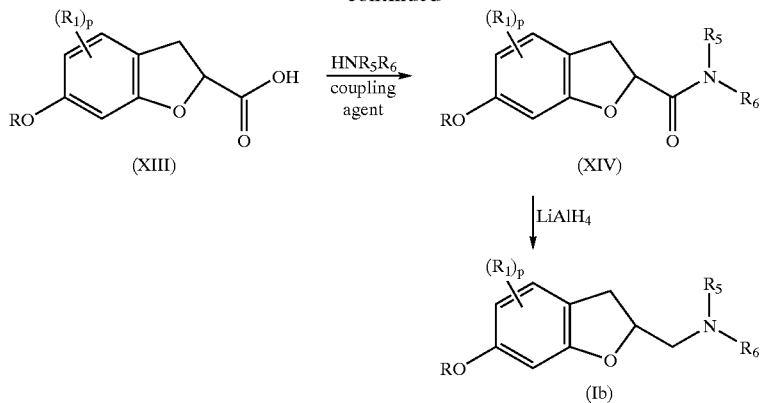

Similarly, compounds of formula I wherein m is 1; n is 0; and ═══ represents a single bond; and $R_2$ is H (Ic) may be prepared by reacting the benzofuran-2-carboxylic acid of formula XII with an amine, $HNR_5R_6$ in the presence of a coupling reagent to give the corresponding benzofuran-2-carboxamide and subsequently reducing said carboxamide to give the desired compound of formula Ic. The reaction is shown in flow diagram IV.

Flow Diagram IV

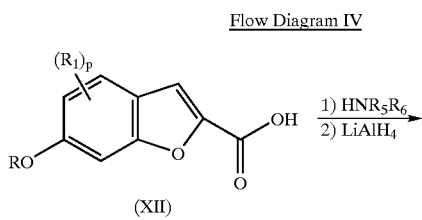

-continued

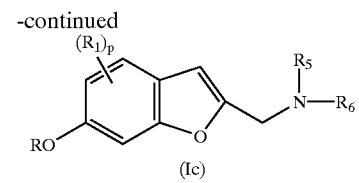

Compounds of formula I wherein m is 2 and ═══ represents a single bond (Id) may be prepared by reacting the appropriate chroman- or dihydrobenzofuranmethanol of formula XV with an oxidizing agent such as dimethyl sulfoxide and oxalyl chloride to give the corresponding 2-carboxaldehyde of formula XVI; reacting said formula XVI carboxaldehyde with a Wittig reagent to give the enol ether of formula XVII; hydrolyzing said enol ether to the methyl carboxaldehyde of formula XVIII; reducing said formula XVIII compound with $NaBH_4$ to give the alcohol of formula XIX and converting said alcohol to the desired product of formula Id using the procedures described hereinabove. The reaction scheme is illustrated in flow diagram V.

Flow Diagram V

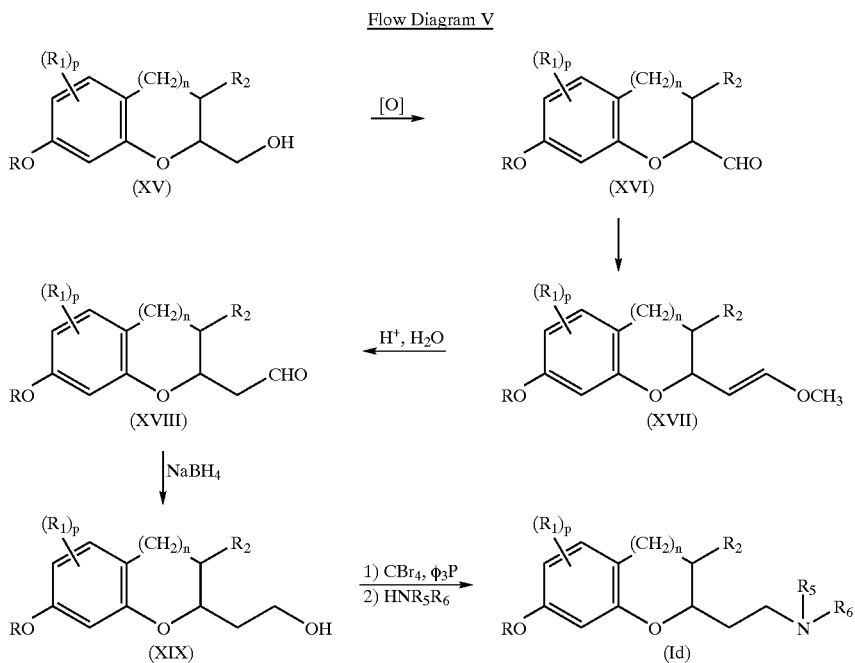

Using these and other conventional methods, compounds of formula I may be prepared from readily available starting materials.

The present invention also provides a convenient and effective process for the preparation of a compound of formula I which comprises reacting a compound of formula II

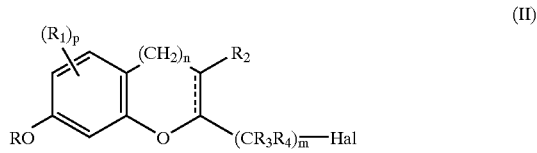

wherein m, n, p, R, $R_1$, $R_2$, $R_3$ and $R_4$ are as defined for formula I and Hal is Cl or Br with an amine, $HNR_5R_6$, at an elevated temperature optionally in the presence of a solvent to give the desired formula I product. The process is illustrated in flow diagram VI.

Flow Diagram VI

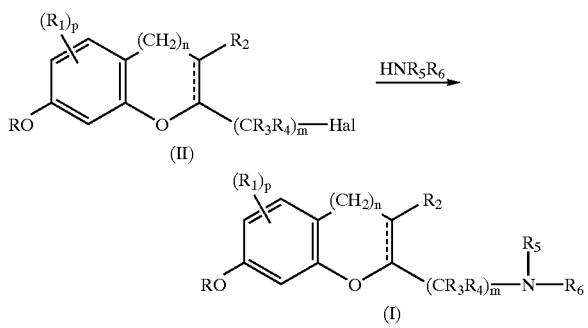

Elevated reaction temperatures suitable for use in the process of the invention range from about 30° C. to the reflux temperature of the solvent or the amine, $HNR_5R_6$.

Suitable solvents include any non-reactive conventional solvent such as acetonitrile, ethyl acetate, diethyl ether, tetrahydrofuran, methylene chloride, toluene, dihalobenzene, dimethylsulfoxide, dimethyl formamide, or the like.

Advantageously, the inventive compound of formula I may be utilized in the treatment of central nervous system disorders relating to or affected by the 5-HT6 receptor such as motor, mood, psychiatric, cognitive, neurodegenerative, or the like disorders; for example, Alzheimer's disease, Parkinson's disease, attention deficit disorder, anxiety, epilepsy, depression, obsessive compulsive disorder, migraine, sleep disorders, feeding disorders (such as anorexia or bulimia), schizophrenia, memory loss, disorders associated with withdrawal from drug abuse, or the like or certain gastrointestinal disorders such as irritable bowel syndrome. Accordingly, the present invention provides a method for the treatment of a disorder of the central nervous system (CNS) related to or affected by the 5-HT6 receptor in a patient in need thereof which comprises providing said patient a therapeutically effective amount of a compound of formula I as described hereinabove. The compounds may be provided by oral or parenteral administration or in any common manner known to be an effective administration of a therapeutic agent to a patient in need thereof.

The therapeutically effective amount provided in the treatment of a specific CNS disorder may vary according to the specific condition(s) being treated, the size, age and response pattern of the patient, the severity of the disorder, the judgment of the attending physician and the like. In general, effective amounts for daily oral administration may be about 0.01 to 1,000 mg/kg, preferably about 0.5 to 500 mg/kg and effective amounts for parenteral administration may be about 0.1 to 100 mg/kg, preferably about 0.5 to 50 mg/kg.

In actual practice, the compounds of the invention are provided by administering the compound or a precursor thereof in a solid or liquid form, either neat or in combination with one or more conventional pharmaceutical carriers or excipients. Accordingly, the present invention provides a pharmaceutical composition which comprises a pharmaceutically acceptable carrier and an effective amount of a compound of formula I as described hereinabove.

Solid carriers suitable for use in the composition of the invention include one or more substances which may also act as flavoring agents, lubricants, solubilizers, suspending agents, fillers, glidants, compression aides, binders, tablet-disintegrating agents or encapsulating materials. In powders, the carrier may be a finely divided solid which is in admixture with a finely divided compound of formula I. In tablets, the formula I compound may be mixed with a carrier having the necessary compression properties in suitable proportions and compacted in the shape and size desired. Said powders and tablets may contain up to 99% by weight of the formula I compound. Solid carriers suitable for use in the composition of the invention include calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Any pharmaceutically acceptable liquid carrier suitable for preparing solutions, suspensions, emulsions, syrups and elixirs may be employed in the composition of the invention. Compounds of formula I may be dissolved or suspended in a pharmaceutically acceptable liquid carrier such as water, an organic solvent, or a pharmaceutically acceptable oil or fat, or a mixture thereof. Said liquid composition may contain other suitable pharmaceutical additives such as solubilizers, emulsifiers, buffers, preservatives, sweeteners, flavoring agents, suspending agents, thickening agents, coloring agents, viscosity regulators, stabilizers, osmo-regulators, or the like. Examples of liquid carriers suitable for oral and parenteral administration include water (particularly containing additives as above, e.g., cellulose derivatives, preferably sodium carboxymethyl cellulose solution), alcohols (including monohydric alcohols and polyhydric alcohols, e.g., glycols) or their derivatives, or oils (e.g., fractionated coconut oil and arachis oil). For parenteral administration the carrier may also be an oily ester such as ethyl oleate or isopropyl myristate.

Compositions of the invention which are sterile solutions or suspensions are suitable for intramuscular, intraperitoneal or subcutaneous injection. Sterile solutions may also be administered intravenously. Inventive compositions suitable for oral administration may be in either liquid or solid composition form.

For a more clear understanding, and in order to illustrate the invention more clearly, specific examples thereof are set forth hereinbelow. The following examples are merely illustrative and are not to be understood as limiting the scope and underlying principles of the invention in any way.

Unless otherwise stated, all parts are parts by weight. The terms NMR and HPLC designate nuclear magnetic resonance and high performance liquid chromatography, respectively. The terms THF, $CH_2Cl_2$ and EtOAc designate tetrahydrofuran, methylene chloride and ethyl acetate, respectively.

EXAMPLE 1

Preparation of Ethyl 7-Hydroxy-4-oxo-4H-1-benzopyran-2-carboxylate

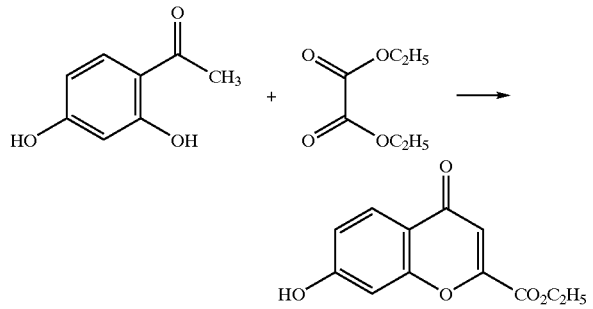

A mixture of 2',4'-dihydroxyacetophone (19.0 g, 0.125 mol) and diethyloxalate (44.8 mL, 0.53 mol) in absolute ethanol is added dropwise to a solution of sodium ethoxide (0.6 mol) in ethanol. The resultant reaction mixture is heated at reflux temperatures, under $N_2$, for 2 hr, cooled to ambient temperatures, poured into a mixture of water and $CH_2Cl_2$ and acidified to pH 3 with 6N HCl. The phases are separated and the organic phase is concentrated to give an oil residue. This residue is dissolved in ethanol and 6N HCl, heated at reflux temperatures for 3 hr, cooled and filtered. The filtercake is air-dried and recrystallized from ethanol/ether to afford the title product as an off-white solid, 19.8 g (68% yield) mp 221–223° C., identified by NMR and mass spectral analyses.

EXAMPLE 2

Preparation of Ethyl 7-Hydroxychroman-2-carboxylate

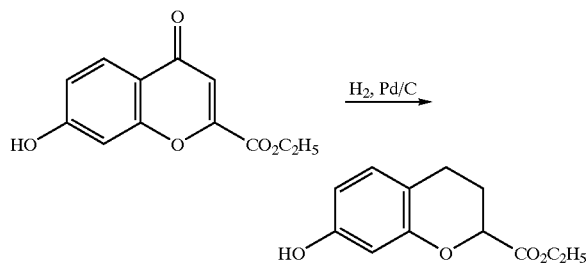

A solution of ethyl 7-hydroxy-4-oxo-4H-1-benzopyran-2-carboxylate (19.0 g, 0.081 mol) in acetic acid is hydrogenated over 10% Pd/C (4.5 g) at 50 psi $H_2$ for 16 hr at ambient temperatures. The catalyst is removed by filtration and the filtrate is concentrated in vacuo to give a residue. The residue is dissolved in EtOAc, washed with saturated $NaHCO_3$, dried over $Na_2SO_4$ and concentrated in vacuo to give a solid residue. Crystallization of the solid from $CCl_4$ affords the title compound as an off-white solid, 17.2 g (96% yield), mp 78–80° C., identified by NMR and mass spectral analyses.

EXAMPLE 3

Preparation of Ethyl 7-(Benzyloxy)chroman-2-carboxylate

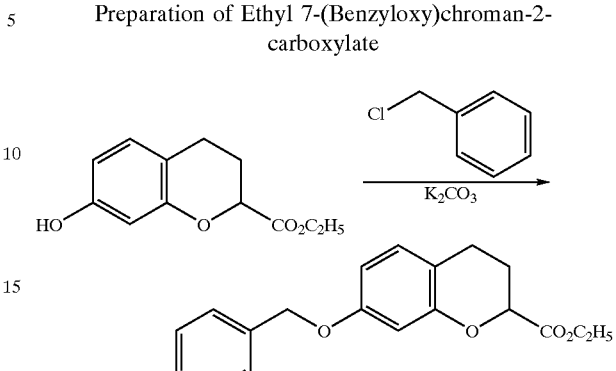

A mixture of ethyl 7-hydroxy-chroman-2-carboxylate (6.1 g, 27.5 mmol), potassium carbonate (7.6 g, 55 mmol), potassium iodide (1.8 g, 11 mmol) and benzyl chloride (3.4 mL, 30 mmol) in acetone is heated at reflux for 16 hr under nitrogen, cooled, concentrated, diluted with water and extracted with EtOAc. The combined extracts are dried over $MgSO_4$ and concentrated to afford the title compound as a straw-colored oil 8.58 g (100% yield), identified by NMR and mass spectral analyses.

EXAMPLE 4

Preparation of [(7-Benzyloxy)chroman-2-yl] methanol

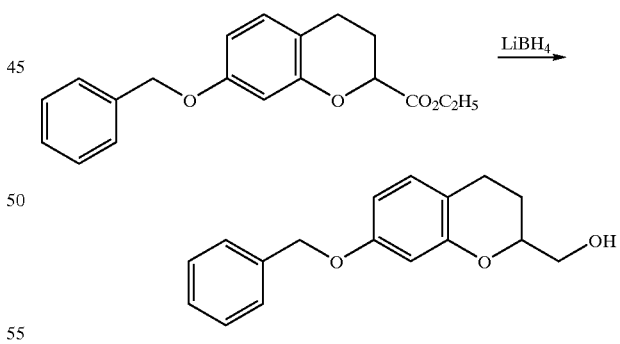

A mixture of ethyl 7-benzyloxy-chroman-2-carboxylate (8.5 g, 27.5 mmol) in anhydrous THF is treated dropwise with lithium borohydride (2.0 M in THF, 65 mmol), stirred at ambient temperature under nitrogen for 16 hr, quenched with methanol, treated with water, and extracted with ether. The extracts are combined, dried over $MgSO_4$ and concentrated to afford the title compound as a colorless oil, 6.9 g (93% yield), identified by NMR and mass spectral analyses.

EXAMPLE 5

Preparation of 2-(Bromomethyl)-7-(benzyloxy)chroman

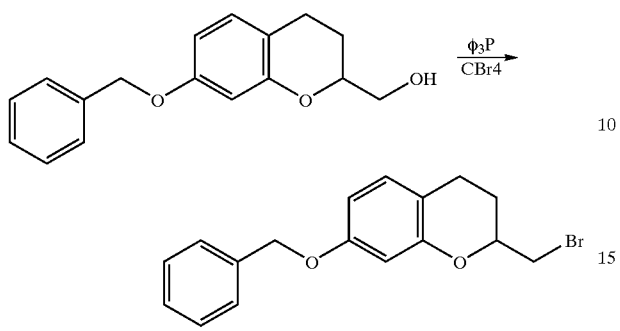

A mixture of [(7-benzyloxy)chroman-2-yl]methanol (8.4 g, 14.8 mmol) and CBr$_4$ (8.5 g, 26 mmol) in CH$_2$Cl$_2$ is treated with a solution of triphenylphosphine (6.6 g, 25 mmol) in CH$_2$Cl$_2$ at 0° C., stirred for 12 hr at 0° C., allowed to warm to room temperature and concentrated in vacuo to give a residue. The residue is purified by column chromatography (silica gel/15% EtOAc in hexane as eluent) to give the title compound as an oil, 4.94 g(100% yield), identified by NMR and mass spectral analyses.

EXAMPLE 6

Preparation of [(7-Benzyloxy)chroman-2-yl]methylamine Hydrochloride

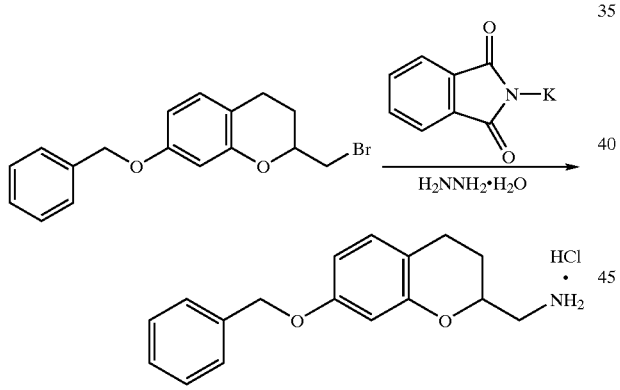

A mixture of 2-(bromomethyl)-7-(benzyloxy)chroman (0.5 g, 1.5 mmol) and potassium phthalimide (0.32 g, 1.7 mmol) in anhydrous dimethyl formamide is heated to 100° C. under N$_2$ for 2 hr, cooled to room temperature and diluted with water. The mixture is extracted with EtOAc. The combined extracts are dried over MgSO$_4$ and concentrated in vacuo. The resultant residue is dissolved in ethanol, treated with hydrazine hydrate (0.15 mL, 3 mmol), heated at reflux temperature for 3 hr, cooled, concentrated, diluted with water and extracted with EtOAc. The combined extracts are dried over MgSO$_4$ and concentrated to afford the free base of the title compound, 0.347 g, (86% yield). Treatment with ethereal HCl affords the HCl salt which is crystallized from ethanol/ether to give the title compound as a beige-colored crystalline powder mp 151–153° C., identified by NMR and mass spectral analyses.

EXAMPLE 7

Preparation of Benzyl-[(7-benzyloxy)chroman-2-yl]methylamine Hydrochloride

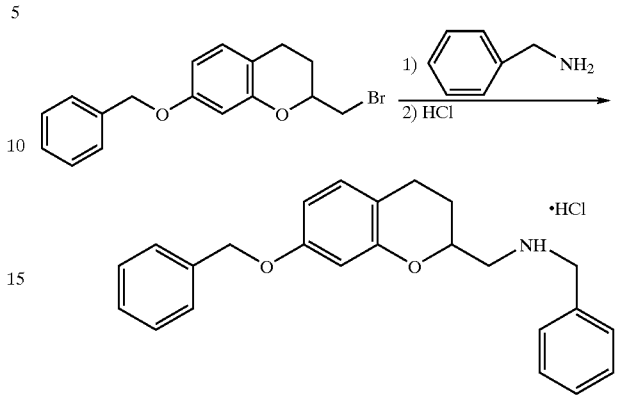

A mixture of 2-(bromomethyl)-7-(benzyloxy)chroman (0.40 g, 1.2 mmol) and benzylamine (1.5 mL, 13.7 mmol) is heated at 100° C. for 2 hr, cooled to room temperature, diluted with water and extracted with CH$_2$Cl$_2$. The combined extracts are concentrated in vacuo to give a residue. The residue is purified by column chromatography (silica gel/5% methanol in chloroform as eluent) to give the free base of the title product, 0.4 g (93% yield). Treatment with etheral HCl affords the title product as a white crystalline powder, mp 177–179° C., identified by NMR and mass spectral analyses.

EXAMPLES 8–17

Preparation of Substituted-[(7-alkoxy)chroman-2-yl]methylamine Hydrochloride

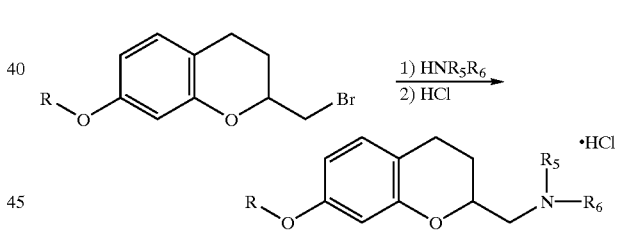

Using essentially the same procedures described in Examples 1 through 7 and substituting the appropriate alkyl halide (R-Hal) as in Example 3 and the appropriate amine (HNR$_5$R$_6$) as in Example 7, the compounds shown in Table I are obtained and identified by NMR and mass spectral analyses.

TABLE I

| Ex. No. | R | R$_5$ | R$_6$ | mp ° C. |
|---|---|---|---|---|
| 8 | benzyl | H | 3-butoxypropyl | 130–132 |
| 9 | benzyl | H | 2-hydroxyethyl | 200–201 |
| 10 | benzyl | H | 3-phenylpropyl | 138–139 |

TABLE I-continued

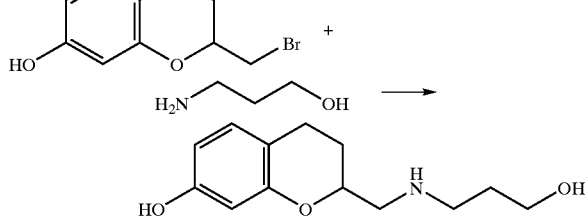

| Ex. No. | R | $R_5$ | $R_6$ | mp ° C. |
|---|---|---|---|---|
| 11 | benzyl | H | 3-(benzyloxy)-propyl | 138–139 |
| 12 | benzyl | H | n-butyl | 150–151 |
| 13 | cyclohexylmethyl | H | 3-hydroxypropyl | 159–160 |
| 14 | 2-chlorobenzyl | H | 3-hydroxypropyl | 114–115 |
| 15 | phenyl | H | 3-hydroxypropyl | 178–179 |
| 18 | naphthalen-2-yl-methyl | H | 3-hydroxypropyl | 151–153 |
| 19 | benzyl | H | 3-hydroxypropyl | 56–57* |

*Free base

EXAMPLE 18

Preparation of 7-(Hydroxychroman-2-yl)methanol

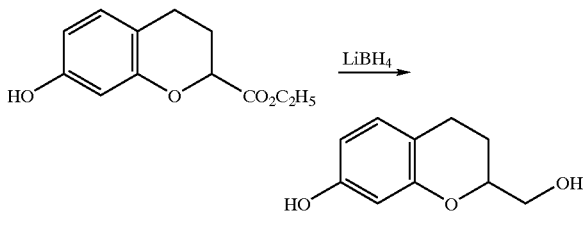

A solution of ethyl 7-hydroxychroman-2-carboxylate (8.0 g, 36 mmol) in THF is treated dropwise with lithium borohydride (2M in THF, 3.5 equiv., 128 mmol), stirred at ambient temperatures, under $N_2$ for 16 hr, quenched with methanol, diluted with water and extracted with ether. The combined extracts are dried over $MgSO_4$ and concentrated in vacuo to afford the title product as a colorless oil, 6.21 g (96% yield), identified by NMR and mass spectral analyses.

EXAMPLE 19

Preparation of 2-(Bromomethyl)-7-hydroxychroman

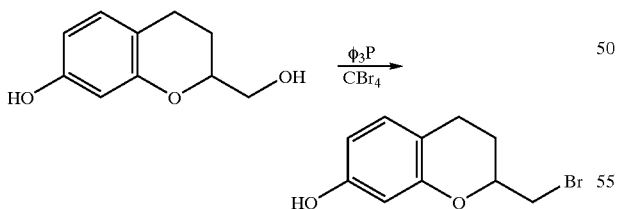

A mixture of (7-hydroxychroman-2-yl)methanol (6.18 g, 34.3 mmol) and $CBr_4$ (19.3 g, 58.3 mmol) in $CH_2Cl_2$ is treated with a solution of triphenylphosphine (9.0 g, 34.3 mmol) in $CH_2Cl_2$ at 0° C., stirred at 0° C. for 6 hr and concentrated in vacuo to give a residue. The residue is purified by column chromatography (silica gel, 60% $CH_2Cl_2$ in hexanes as eluent) to give the title product as an oil, 4.61 g (55% yield), identified by NMR and mass spectral analyses.

EXAMPLE 20

Preparation of 3-[(7-hydroxychroman-2-ylmethyl)amino]propan-1-ol

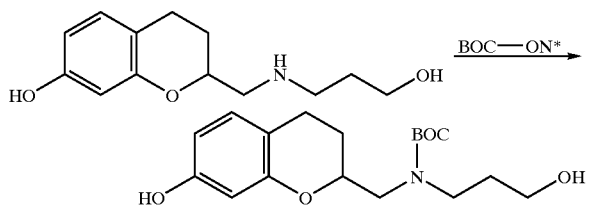

A mixture of 2-bromomethyl-7-hydroxychroman (4.57 g, 18.8 mmol) and 3-amino-1-propanol (18.3 mL, 240 mmol) is heated at 100° C. for 2 hr, cooled, diluted with water and extracted with $CH_2Cl_2$. The combined extracts are concentrated in vacuo to give a residue. The residue is purified by column chromatography (silica gel/5% methanol in $CH_2Cl_2$ as eluent) to give the title product as a clear oil, 3.27 g (73% yield) identified by NMR and mass spectral analyses.

EXAMPLE 21

Preparation of (N-t-Butoxycarbonyl)-3-[(7-hydroxychroman-2-ylmethyl)amino]propan-1-ol

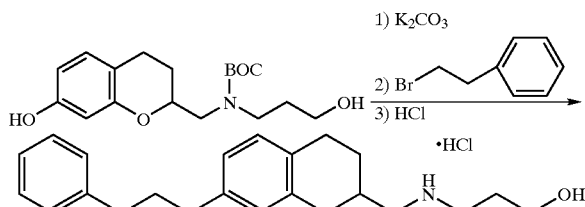

A mixture of 3-[(7-hydroxychroman-2-ylmethyl)amino]propan-1-ol (2.82 g, 11.9 mmol) and triethylamine (1.82 g, 18 mmol) in dioxane is treated with BOC-ON* (3.52g, 11.9 mmol), stirred at room temperature for 24 hr and concentrated in vacuo. The resultant residue is purified by column chromatography (silica gel/2% methanol in $CH_2Cl_2$ as eluent) to give the title product as a clear oil, 3.17 g (79% yield), identified by NMR and mass spectral analyses.

*2-(t-butoxycarbonyloxyimino)-2-phenylacetonitrile manufactured by Aldrich, St. Louis, Mo.

EXAMPLE 22

Preparation of 3-{[(7-(Phenethyloxy)chroman-2-ylmethyl]amino}propan-1-ol Hydrochloride A mixture of (N-t-butoxycarbonyl)-3-[(7-hydroxychroman-2-ylmethyl)amino]propan-1-ol (0.365 g, 1.08 mmol) $K_2CO_3$ (0.299 g, 2.16 mmol), KI (0.083 g, 0.05 mmol) and phenethylbromide (0.18 mL, 1.3 mmol) in acetone is heated at reflux temperature under $N_2$, for 12 hr, cooled to room temperature, concentrated, diluted with water and extracted with EtOAc. The combined extracts are dried over $MgSO_4$ and concentrated in vacuo to give an oil residue. This residue is purified by column chromatography (silica gel/35% EtOAc in hexanes as eluent) to give the BOC-protected free base of the title product as a clear oil, 0.278 g (56% yield). Treatment with 4N HCl in dioxane filtration and recrystallization of the filtercake from ethanol/ether affords the title product as an off-white solid, 0.182 g (77% yield) mp 970–100° C., identified by NMR and mass spectral analyses.

EXAMPLES 23 and 24

Preparation of 3{[(7-Substituted)chroman-2-ylmethyl]amino}propan-1-ol Salt

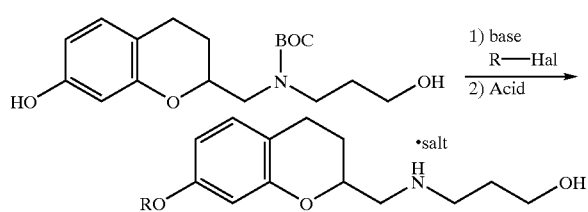

Using essentially the same procedure described in Example 22 and substituting the appropriate alkylhalide and acid, the compounds shown in Table II are obtained and identified by NMR and mass spectral analyses.

TABLE II

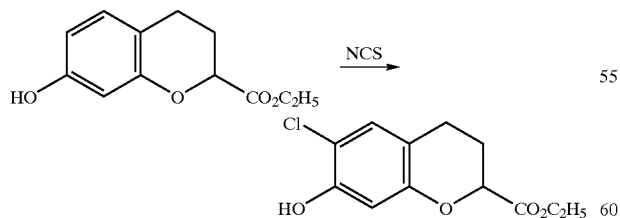

| Ex. No. | R | Salt | mp ° C. |
|---|---|---|---|
| 23 | 2-methylthiazol-4-ylmethyl | $CF_3CO_2H$ | 94–102 |
| 24 | 2-methylthiazol-4-ylmethyl | HCl | 123–128 |

EXAMPLE 25

Preparation of Ethyl 6–Chloro-7-hydroxychroman-2-carboxylate

A solution of ethyl 7-hydroxychroman-2-carboxylate (5.0 g, 22.5 mmol) in THF is treated with N-chlorosuccinimide (NCS) (3.6 g, 27 mmol), stirred for 40 hr and concentrated in vacuo. The resultant residue is purified chromatographically (silica gel/20% EtOAc in hexanes as eluent) to give the title product, 3.0 g (52% yield), identified by NMR and mass spectral analyses.

EXAMPLE 26

Preparation of Methyl 7-Benzyloxy-6-chlorochroman-2-carboxylate

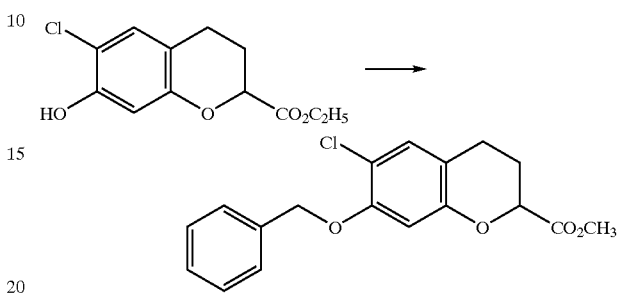

A solution of ethyl 6-chloro-7-hydroxychroman-2-carboxylate (3.0 g, 11.7 mmol) in THF is treated with NaH (3.0 equiv, 35 mmol) at 0° C., stirred for 20 minutes, treated with benzylbromide (3.0 g, 17.5 mmol), stirred for 16 hr, concentrated and diluted with water and EtOAc. The aqueous phase is separated, acidified to pH 1–2 with 2N HCl and extracted with EtOAc. The extracts are combined, dried over $MgSO_4$ and concentrated in vacuo. The resultant residue is dissolved in methanol, treated with a catalytic amount of p-toluenesulfonic acid, heated at reflux temperature for 18 hr, cooled and concentrated in vacuo. This resultant residue is triturated under EtOAc/hexanes and filtered. The filtercake is further purified by short-column chromatography (silica gel, 5:1 hexane:EtOAc as eluent) to afford the title product as a light yellow solid, 2.7 g (6.9% yield), identified by NMR and mass spectral analyses.

EXAMPLE 27

Preparation of 7-Benzyloxy-6-chlorochroman-2-ylmethanol

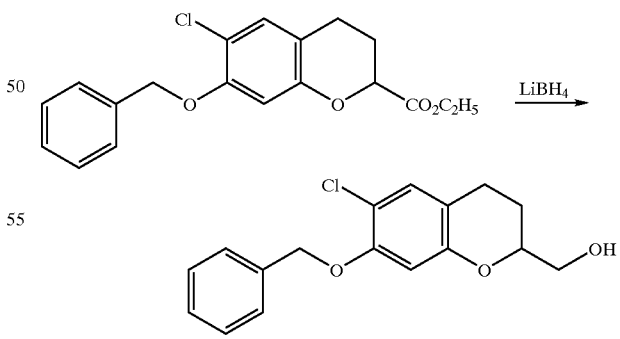

Using essentially the same procedure described in Example 4 and employing ethyl 7-benzyl-6-chlorochroman-2-carboxylate (1.56 g, 4.7 mmol) as substrate, the title product is obtained as a colorless oil, 1.53 g (100% yield), identified by NMR and mass spectral analyses.

EXAMPLE 28

Preparation Of 7-Benzyloxy-2-bromomethyl-6-chlorochroman

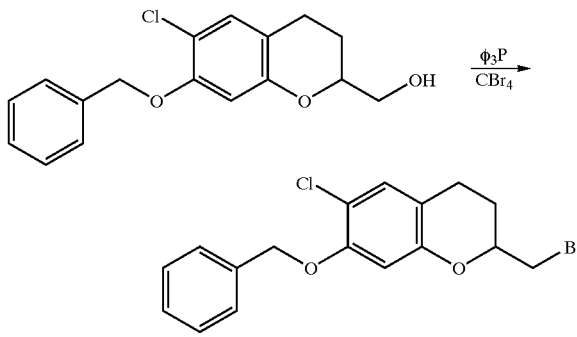

Using essentially the same procedure described in Example 5 and employing 7-benzyloxy-6-chlorochroman-2-ylmethanol (2.59 g, 7.8 mmol) as substrate, the title product is obtained as a yellow oil, identified by NMR and mass spectral analyses.

EXAMPLE 29

Preparation of 3-{[(7-Benzyloxy)-6-chlorochroman-2-ylmethyl]amino}propan-1-ol Fumaric Acid Salt

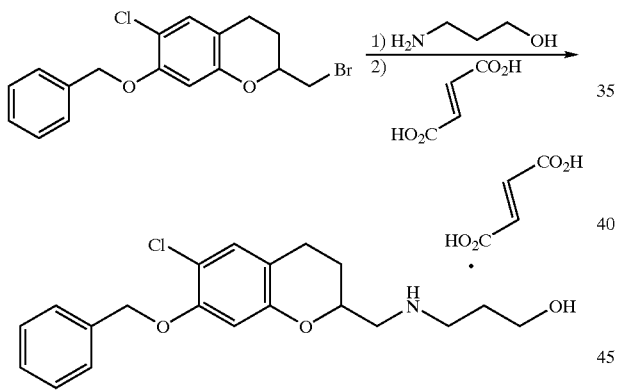

Using essentially the same procedure described in Example 7 and employing 7-benzyloxy-2-bromomethyl-6-chlorochroman as substrate and fumaric acid as the acid, the title product is obtained as a white powder, mp 148–150° C., identified by NMR and mass spectral analyses.

EXAMPLE 30

Preparation of 3-{[(7-benzyloxy)chroman-2-ylmethyl]methylamino}propan-1-ol Fumaric Acid Salt

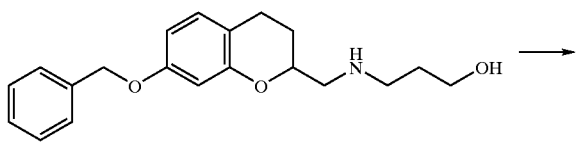

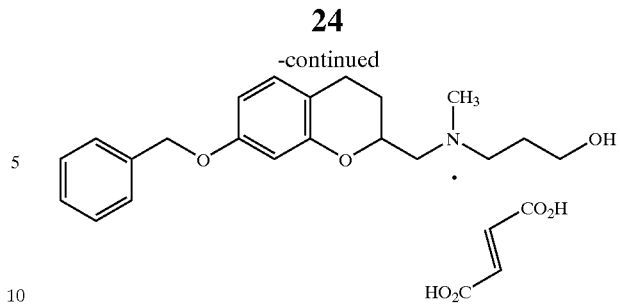

A mixture of 3-((7-benzyloxy-chroman-2-ylmethyl)-amino]-propan-1-ol (4.4 g, 13.4 mmol) and $NaHCO_3$ (1.13 g, 13.4 mmol in 20 mL water) in chloroform is treated with di-t-butyl dicarbonate (2.93 g, 13.4 mmol), heated at reflux temperature for 1.5 hours and cooled. The layers are separated, the organic phase is dried over $MgSO_4$ and concentrated to afford the BOC-protected compound as a colorless oil (6.0 g, 100% yield). A portion of this compound (1.24 g, 2.9 mmol) is dissolved in THF, treated dropwise with lithium aluminum hydride (1 M in THF, 35 mL, 35 mmol), heated at reflux temperature under nitrogen for 16 hr, cooled to ambient temperature, treated with saturated $NH_4Cl$ and filtered. The filtrate is dried over $MgSO_4$ and concentrated to provide the free base of the title compound. Treatment of the free base with one equivalent of an ethanolic solution of fumaric acid affords the title product as a white amorphous solid, 0.98g (74% yield) mp 100–106° C., identified by NMR and mass spectral analyses.

EXAMPLES 31–37

Preparation of 7-Oxychroman-2-ylalkylamine Derivatives

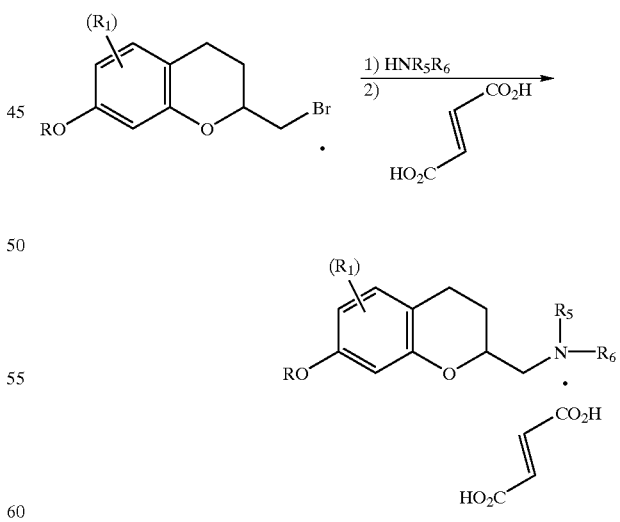

Using essentially the same procedures described hereinabove and employing the appropriate substrate and amine, the compounds in Table III are obtained and identified by NMR and mass spectral analyses.

TABLE III

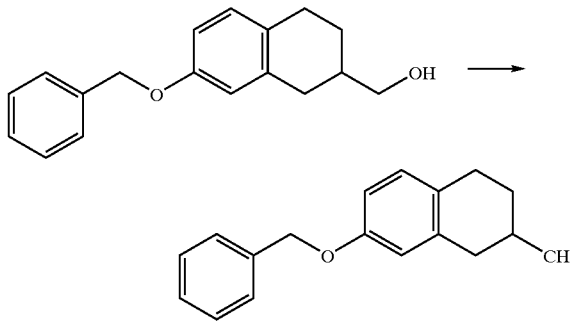

| Ex. No. | R | $R_1$ | $R_5$ | $R_6$ | mp ° C. |
|---|---|---|---|---|---|
| 31 | benzyl | H | H | 2-(benzylsulfonyl)-ethyl | 81–85 |
| 32 | benzyl | H | H | 3-(4-nitrophenoxy)-propyl | 118–120 |
| 33 | benzyl | H | H | 3-(3-nitrophenoxy)-propyl | 82–87 |
| 34 | benzyl | H | H | 3-(3-chlorophenoxy)-propyl | 110–116 |
| 35 | benzyl | H | H | 3-(7-coumarinoxy)-propyl | 63–68 |
| 36 | benzyl | 6-Cl | H | 3-(7-coumarinoxy)-propyl | 92–95 |
| 37 | benzyl | H | H | (R)-2-[3-benzylthio)-1-hydroxy]propyl | 59–65 |

EXAMPLE 38

Preparation of 7-[(Benzyloxy)chroman-2-yl] carboxaldehyde

A solution of oxalyl chloride (1.75 mL, 20 mmol) in $CH_2Cl_2$ is treated dropwise with a mixture of dimethylsulfoxide (1.9 mL, 27 mmol) in $CH_2Cl_2$ at −78° C., stirred for 10 minutes, treated slowly with a solution of [7-(benzyloxy)chroman-2-yl]methanol (3.6 g, 13.5 mmol) in $CH_2Cl_2$, stirred for 20 minutes, treated with diisopropyl ethylamine (14 mL, 81 mmol), stirred for 0.5 hr at −78° C., allowed to warm to ambient temperatures, poured onto dilute aqueous $NH_4Cl$ and extracted with $CH_2Cl_2$. The combined extracts are dried over $MgSO_4$ and concentrated in vacuo. The resultant residue is chromatographed (silica gel/20% EtOAc in hexanes as eluent) to afford the title compound, 1.8 g (50% yield), identified by NMR and mass spectral analyses.

EXAMPLE 39

Preparation of 7-(Benzyloxy)-2-[2-methoxyethenyl] chroman

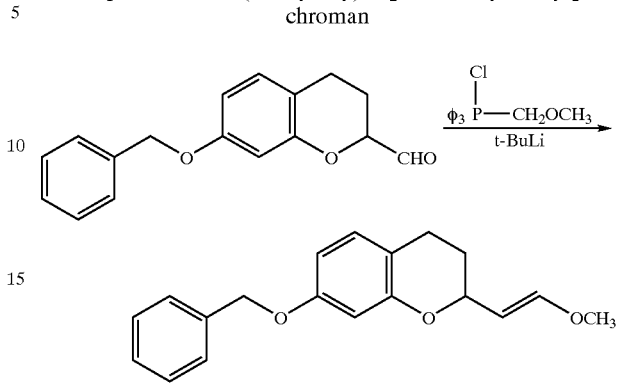

A suspension of (methoxymethyl)triphenylphosphonium chloride (6.9 g, 20 mmol) in diethyl ether is treated with t-butyl lithium (1.7 M in pentane, 10.3 mL, 17.5 mmol) at 0° C., stirred for 15 minutes, treated dropwise with an ethereal solution of 7-[(benzyloxy)chroman-2-yl] carboxaldehyde (1.8 g, 6.7 mmol), stirred for 5 hr, poured into saturated $NaHCO_3$ and extracted with EtOAc. The combined extracts are dried over $MgSO_4$ and concentrated in vacuo. The resultant residue is chromatographed (silica gel/50% EtOAc in hexanes as eluent) to give the title compound, 1.38 g (70% yield), identified by NMR and mass spectral analyses.

EXAMPLE 40

Preparation of [7-(Benzyloxy)-3,4-dihydro-2H-chromen-2-yl]acetaldehyde

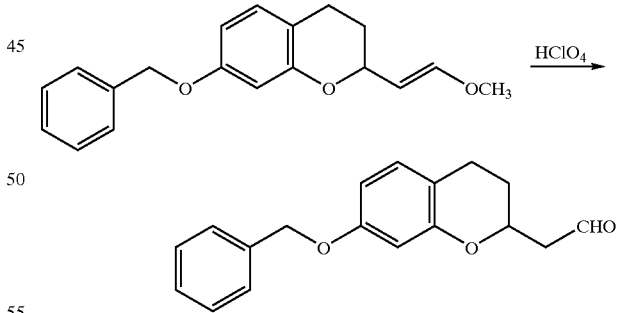

A solution of 7-(benzyloxy)-2-[2-methoxyethenyl]-chroman (1.0 g, 3.3 mmol) in THF is treated with perchloric acid (0.3 ml), stirred at room temperature for 15 minutes, poured into dilute $NH_4OH$ and extracted with ether. The combined extracts are dried over $MgSO_4$ and concentrated in vacuo. The resultant residue is chromatographed (silica gel/20% EtOAc in hexanes as eluent) to give the title product as a colorless oil, 0.484 g (50% yield), identified by NMR and mass spectral analyses.

EXAMPLE 41

Preparation of 7-(Benzyloxy)-2-(2-bromoethyl) chroman

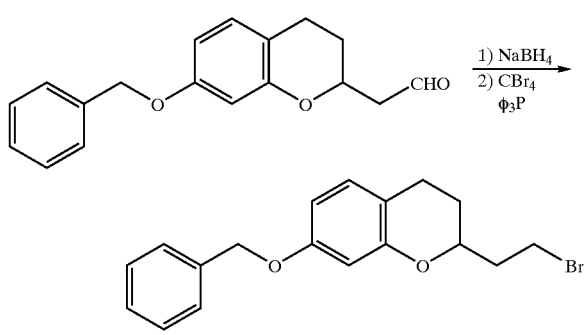

A solution of 7-(benzyloxy)-3,4-dihydro-2H-chromen-2-yl]acetaldehyde (0.334 g, 1.18 mmol) in methanol is treated, with stirring, with NaBH$_4$ (0.090 g, 2.4 mmol) at room temperature under N$_2$, stirred for 1 hr, diluted with water and extracted with ether. The combined extracts are dried over MgSO$_4$ and concentrated in vacuo to give the corresponding 2-ethanol as a colorless oil, 0.32 g (95% yield) identified by NMR and mass spectral analyses. This oil is dissolved in CH$_2$Cl$_2$, cooled to 0° C., treated with CBr$_4$ (0.66 g, 2 mmol) and triphenylphosphine (0.50 g, 1.9 mmol), stirred for 16 hr and concentrated in vacuo. The resultant residue is chromatographed (silica gel/15% EtOAc in hexanes as eluent) to give the title product as a light yellow oil, 0.386 g (100% yield), identified by NMR and mass spectral analyses.

EXAMPLE 42

Preparation of 3-{[2-(7-Benzyloxy)chroman-2-yl]ethylamino}propan-1-ol Hydrochloride

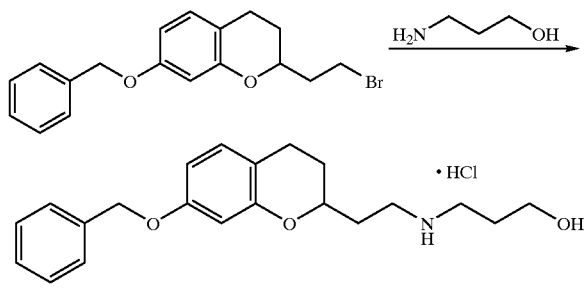

Using essentially the same procedure described in Example 7 and employing 7-(benzyloxy)-2-(2-bromoethyl) chroman (0.38 g, 1.1 mmol) and 3-amino-1-propanol (0.84 mL, 11 mmol) the free base of the title product is obtained, 0.317 g (84% yield). Treatment with ethereal HCl affords the title product as a light beige crystalline powder, mp 162°–164° C., identified by NMR and mass spectral analyses.

EXAMPLE 43

Preparation of Ethyl (R)-7-Hyroxychroman-2-carboxylate

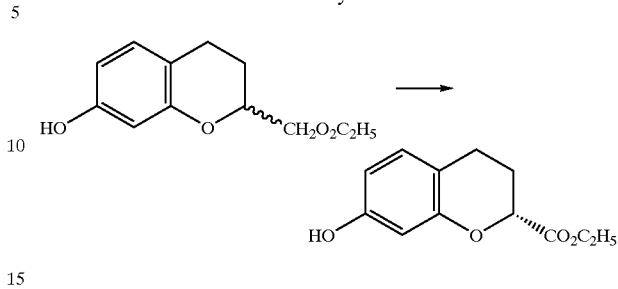

A mixture of racemic ethyl 7-hydroxy-2-carboxylate (2.2 g, 10 mmol) in water, THF and pH7 phosphate buffer is treated with chirazyme L-6 (40 mg) with vigorous stirring. The reaction is monitored by HPLC (chiracel AD, 25×0.46 cm, hexanes:ethanol 3:65 plus 0.1% trifluoroacetic acid, 0.7 mL/min., wavelength 278 nm). When the reaction is complete, the mixture is extracted with EtOAc. The combined extracts are washed sequentially with saturated NaHCO$_3$ and brine, dried over MgSO$_4$ and concentrated in vacuo to afford the title product as a white crystalline solid, 1.1 g (100% yield), 100% ee, identified by NMR and mass spectral analyses.

EXAMPLES 44–46

Preparation of (R)-7[(Benzyloxy)chroman-2-yl] methylamino Derivatives

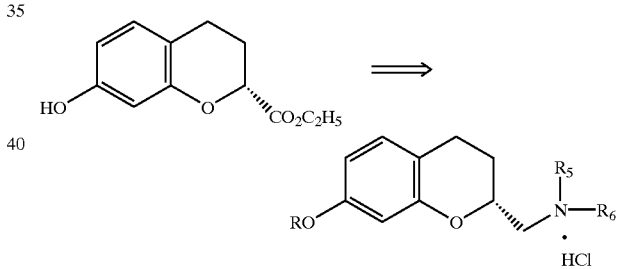

Using essentially the same procedures described hereinabove and employing ethyl (R)-7-hydroxychroman-2-carboxylate as starting material, the chiral compounds shown in Table IV are obtained and identified by NMR mass spectral analyses.

TABLE IV

| Ex. No. | R | R$_5$ | R$_6$ | mp ° C. |
|---|---|---|---|---|
| 44 | benzyl | H | 2-hydroxyethyl | 196–197 |
| 45 | benzyl | H | 3-hydroxypropyl | 119 |
| 46 | benzyl | H | 3-methoxypropyl | 128–129 |

EXAMPLE 47

Preparation of 4-(Benzyloxy)-2-hydroxybenzaldehyde

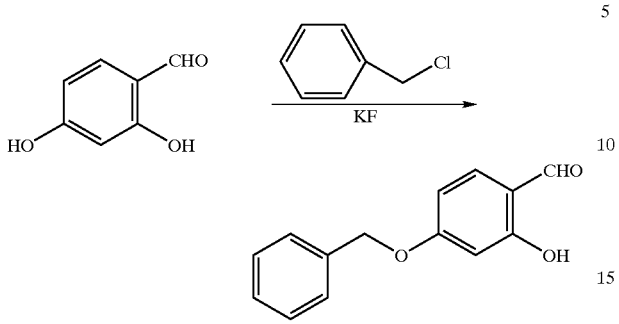

A solution of 2,4-dihydroxybenzaldehyde (20 g, 0.144 mol), potassium flouride (16.7 g, 2 equivalents) and benzyl chloride (29 mL, 1.75 equivalents) in acetonitrile (150 mL) is heated at reflux temperature for 16 hr, cooled to room temperature, concentrated, diluted with water and extracted with EtOAc. The combined extracts are dried over $MgSO_4$ and concentrated in vacuo to give an oil residue. The residue is chromatographed (silica gel/10% EtOAc in hexanes to 50% EtOAc in hexanes as gradient eluents) to give the title product as a white solid, 25.9 g, identified by NMR and mass spectral analyses.

EXAMPLE 48

Preparation of 6-(Benzyloxy)benzofuran-2-carboxylic Acid

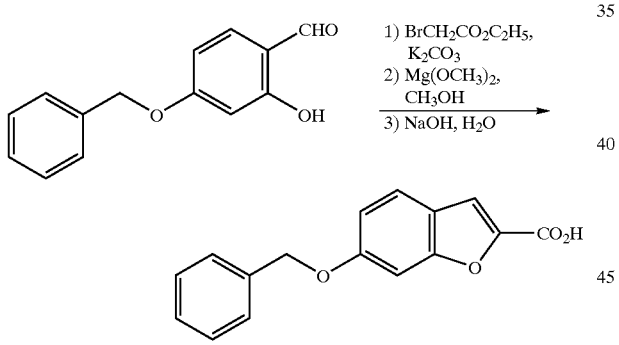

A mixture of 2-hydroxy-4-benzyloxybenzaldehyde (18.26 g, 80 mmol), ethyl bromoacetate (7.6 mL, 1 equivalent) and potassium carbonate (17.7 g, 1.6 equivalents) in acetone is heated at reflux temperature for 16 hr, cooled to room temperature, concentrated, diluted with water and extracted with EtOAc. The combined extracts are dried over MgSO, and concentrated in vacuo to give the corresponding 2-oxymethylcarboxylate as a light yellow solid, 17.7 g (73% yield). This solid is dissolved in methanolic magnesium methoxide (7.4% solution, 300 mL), heated at reflux temperature for 2 hr, concentrated, diluted with water and extracted with EtOAc. The combined extracts are dried over $MgSO_4$ and concentrated in vacuo to give the corresponding ring closed benzofuran-2-carboxylate ester as a viscous oil, 11.4 g (68% yield). This oil (5.0 g, 17.7 mmol) is dissolved in methanol, treated with aqueous NaOH (2.5N, 50 mL) heated at reflux temperature for 0.5 hr, concentrated to half-volume, cooled to room temperature, acidified with HCl and filtered. The filtercake is air-dried to give the title product as a pale yellow solid, 4.7 g, (99% yield) mp 199–201° C., identified by NMR and mass spectral analyses.

EXAMPLE 49

Preparation of 6-(Benzyloxy)-2,3-dihydrobenzofuran-2-carboxylic Acid

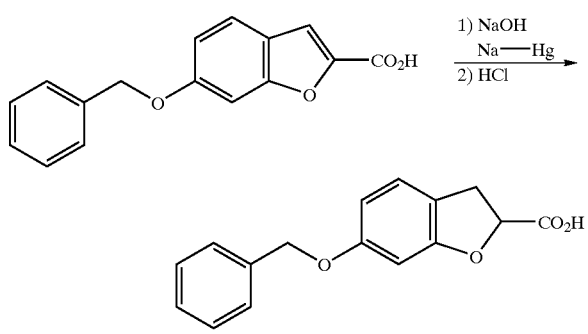

A solution of 6-(benzyloxy)benzofuran-2-carboxylic acid (3.4 g, 12.6 mmol) in aqueous NaOH (2.5N, 40 mL) is treated with 6% Na—Hg (20 g), stirred for 16 hr, allowed to stand without stirring and decanted. The supernatant is acidified with HCl and filtered. The filtercake is air-dried to afford the title product as a white solid, 2.2 g (64% yield) mp 118–119° C., identified by NMR and mass spectral analyses.

EXAMPLE 50

Preparation of 6-(Benzyloxy)-2,3-dihydrobenzofuran-2-(2-hydroxyethyl)carboxamide

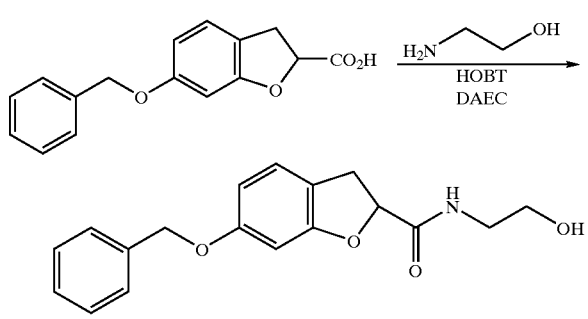

A mixture of 6-(benzyloxy)-2,3-dihydrobenzofuran-2-caroboxylic acid (0.70 g, 2.58 mmol), 1-hydroxybenzotriazole hydrate (HOBT) 0.56 g, 1.6 equiv.) and 1-[3-(dimethylamino)propyl]-3-ethylcarbodiimide hydrochloride (DAEC) (0.55 g, 1.1 equiv.) in dimethyl. formamide at 0° C. is treated with 2-aminoethanol (0.17 mL, 2.8 mmol), stirred for 16 hr, diluted with water and extracted with EtOAc. The combined extracts are dried over $MgSO_4$ and concentrated in vacuo to give the title product as a pale yellow oil, 0.75 g, identified by NMR and mass spectral analyses.

EXAMPLE 51

Preparation of 2-{[6-(Benzyloxy)-2,3-dihydrobenzofuran-2-ylmethyl]amino}ethanol Hydrochloride

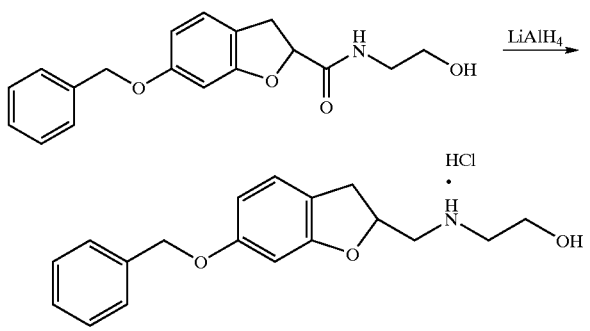

A solution of 6-(benzyloxy)-2,3-dihydrobenzofuran-2-(2-hydroxyethyl)carboxamide (0.25 g, 0.79 mmol) in THF is treated with LiAlH$_4$ (1.0 M in THF, 3.2 mL, 4 equiv), heated at reflux temperature for 4 hr, cooled to room temperature, quenched with saturated NH$_4$Cl solution, diluted with water and extracted with EtOAc. The combined extracts are dried over MgSO$_4$ and concentrated in vacuo to afford the free base of the title product as a white solid, 0.23 g (100% yield). Treatment with ethereal HCl gives the title product as a white powder, mp 161–163° C., identified by NMR and mass spectral analyses.

EXAMPLES 52–55

Preparation of 6-Alkoxy-2-(methylamino) benzofuran Derivatives

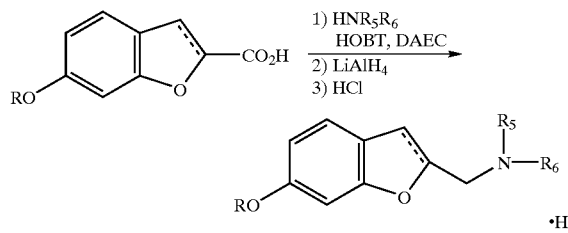

Using essentially the same procedures described hereinabove and employing the appropriate benzofuran-2-yl- or dihydrobenzofuran-2-yl-carboxylic acid and an appropriate amine, the compounds shown in Table V are obtained and identified by NMR and mass spectral analyses.

TABLE V

| Ex. No. | R | bond | R$_5$ | R$_6$ | mp ° C. |
|---|---|---|---|---|---|
| 52 | benzyl | Single | H | H | 237–238 |
| 53 | benzyl | Single | H | 3-hydroxypropyl | 125–127 |
| 54 | benzyl | Double | H | benzyl | 198–200 |
| 55 | benzyl | Double | H | 3-hydroxypropyl | 145–147 |

EXAMPLE 56

Comparative Evaluation of 5-HT6 Binding Affinity of Test Compounds

The affinity of test compounds for the serotonin 5-T6 receptor is evaluated in the following manner. Cultured Hela cells expressing human cloned 5-HT6 receptors are harvested and centrifuged at low speed (1,000×g) for 10.0 min to remove the culture media. The harvested cells are suspended in half volume of fresh physiological phosphate buffered saline solution and recentrifuged at the same speed. This operation is repeated. The collected cells are then homogenized in ten volumes of 50 mM Tris.HCl (pH 7.4) and 0.5 mM EDTA. The homogenate is centrifuged at 40,000×g for 30.0 min and the precipitate is collected. The obtained pellet is resuspended in 10 volumes of Tris.HCl buffer and recentrifuged at the same speed. The final pellet is suspended in a small volume of Tris.HCl buffer and the tissue protein content is determined in aliquots of 10–25 μl volumes. Bovine Serum Albumin is used as the standard in the protein determination according to the method described in Lowry et al., *J. Biol. Chem.*, 193:265 (1951). The volume of the suspended cell membranes is adjusted to give a tissue protein concentration of 1.0 mg/ml of suspension. The prepared membrane suspension (10 times concentrated) is aliquoted in 1.0 ml volumes and stored at −70° C. until used in subsequent binding experiments.

Binding experiments are performed in a 96 well microtiter plate format, in a total volume of 200 μl. To each well is added the following mixture: 80.0 μl of incubation buffer made in 50 mM Tris.HCl buffer (pH 7.4) containing 10.0 mM MgCl$_2$ and 0.5 mM EDTA and 20 μl of [$^3$H]-LSD (S.A., 86.0 Ci/mmol, available from Amersham Life Science), 3.0 nM. The dissociation constant, K$_D$ of the [$^3$H]LSD at the human serotonin 5-HT6receptor is 2.9 nM, as determined by saturation binding with increasing concentrations of [$^3$H] LSD. The reaction is initiated by the final addition of 100.0 μl of tissue suspension. Nonspecific binding is measured in the presence of 10.0 μM methiothepin. The test compounds are added in 20.0 μl volume.

The reaction is allowed to proceed in the dark for 120 min at room temperature, at which time, the bound ligand-receptor complex is filtered off on a 96 well unifilter with a Packard Filtermate® 196 Harvester. The bound complex caught on the filter disk is allowed to air dry and the radioactivity is measured in a Packard TopCount® equipped with six photomultiplier detectors, after the addition of 40.0 μl Microscint®-20 scintillant to each shallow well. The unifilter plate is heat-sealed and counted in a PackardTopCount® with a tritium efficiency of 31.0%.

Specific binding to the 5-HT6 receptor is defined as the total radioactivity bound less the amount bound in the presence of 10.0 μM unlabeled methiothepin. Binding in the presence of varying concentrations of test compound is expressed as a percentage of specific binding in the absence of test compound. The results are plotted as log % bound versus log concentration of test compound. Nonlinear regression analysis of data points with a computer assisted program Prisms yielded both the IC$_{50}$ and the K$_i$ values of test compounds with 95% confidence limits. A linear regression line of data points is plotted, from which the IC$_{50}$ value is determined and the K$_i$ value is determined based upon the following equation:

$$K_i = IC_{50}/(1+L/K_D)$$

where L is the concentration of the radioactive ligand used and K$_D$ is the dissociation constant of the ligand for the receptor, both expressed in nM.

Using this assay, the following Ki values are determined and compared to those values obtained by representative compounds known to demonstrate binding to the 5-HT6 receptor. The data are shown in Table VI, below.

TABLE VI

| Test Compound (Ex. No.) | 5-HT6 Binding Ki (nM) |
|---|---|
| 6 | 15 |
| 7 | 26 |
| 8 | 16 |
| 9 | 12 |
| 10 | 44 |
| 11 | 27 |
| 12 | 43 |
| 13 | 357 |
| 14 | 38 |
| 15 | 283 |
| 16 | 30 |
| 17 | 13 |
| 22 | 101 |
| 23 | 41 |
| 24 | 120 |
| 29 | 34 |
| 30 | 27 |
| 31 | 125 |
| 32 | 157 |
| 33 | 69 |
| 34 | 192 |
| 35 | 29 |
| 36 | 43 |
| 37 | 303 |
| 42 | 107 |
| 44 | 10 |
| 45 | 9 |
| 46 | 25 |
| 51 | 386 |
| 52 | 158 |
| 53 | 339 |
| 54 | 1353 |
| 55 | 1181 |
| Comparative Examples | |
| Clozapine | 6.0 |
| Loxapine | 41.4 |
| Bromocriptine | 23.0 |
| Methiothepin | 8.3 |
| Mianserin | 44.2 |
| Olanzepine | 19.5 |

As can be seen from the results set forth above, the compounds of the present invention demonstrate affinity for the 5-HT6 receptor.

What is claimed is:

1. A compound of formula I

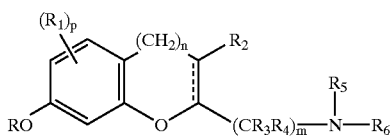

(I)

wherein
R is a substituted $C_1$–$C_6$alkyl group, or an aryl or heteroaryl group each optionally substituted;
$R_1$ is halogen, CN, $OR_7$, $CO_2R_8$, $CONR_9R_{10}$, $SO_xR_{11}$ or a $C_1$–$C_6$alkyl, $C_2$–$C_6$alkenyl, $C_2$–$C_6$alkynyl, $C_3$–$C_6$cycloalkyl, cyclohetereoalkyl, phenyl or heteroaryl group each optionally substituted;
$R_2$ $R_3$ and $R_4$ are each independently H or an optionally substituted $C_1$–$C_6$ alkyl group with the proviso that when R is a substituted $C_1$–$C_6$alkyl group then $R_2$, $R_3$ and $R_4$ must be H;
$R_5$ and $R_6$ are each independently H or a $C_1$–$C_6$alkyl, $C_3$–$C_6$cycloalkyl or heterocyclylalkyl group each optionally substituted or $R_5$ and $R_6$ may be taken together with the atom to which they are attached to represent a 3- to 10-membered optionally substituted mono- or bicyclic ring system optionally containing one or two additional heteroatoms selected from N, O or S with the proviso that when R is a substituted $C_1$–$C_6$alkyl group then $R_5$ and $R_6$ must be other than a $C_3$–$C_6$cycloalkyl or cycloheteroalkyl group;
m is an integer of 1, 2, 3 or 4;
n is 0 or 1;
p is 0 or an integer of 1, 2 or 3;
=== represents a single bond or a double bond;
x is 0 or an integer of 1 or 2;
$R_7$ is H, $CO_2R_{12}$ or a $C_1$–$C_6$alkyl, $C_2$–$C_6$alkenyl, $C_2$–$C_6$alkynyl, aryl or heteroaryl group each optionally substituted;
$R_8$ and $R_{12}$ are each independently H or a $C_1$–$C_6$alkyl, $C_2$–$C_6$alkenyl, $C_2$–$C_6$alkynyl, $C_3$–$C_6$cycloalkyl, cycloheteroalkyl, aryl or heteroaryl group each optionally substituted;
$R_9$ and $R_{10}$ are each independently H or an optionally substituted $C_1$–$C_6$alkyl group; and
$R_{11}$ is a $C_1$–$C_6$alkyl, aryl or heteroaryl group each optionally substituted; or
the stereoisomers thereof or a pharmaceutically acceptable salt thereof.

2. The compound according to claim 1 wherein R is a substituted $C_1$–$C_6$alkyl group.

3. The compound according to claim 1 wherein n is 1 and === represents a single bond.

4. The compound according to claim 1 wherein m is 1.

5. The compound according to claim 2 wherein $R_5$ and $R_6$ are each independently H or an optionally substituted $C_1$–$C_6$alkyl group.

6. The compound according to claim 3 wherein m is 1; p is 0 or 1; and $R_2$ is H.

7. The compound according to claim 4 wherein n is 0 and === represents a single bond.

8. The compound according to claim 6 wherein R is benzyl and $R_5$ and $R_6$ are each independently H or $C_1$–$C_6$alkyl optionally substituted with hydroxy.

9. The compound according to claim 5 selected from the group consisting of:
[3-(benzoxazol-6-yloxy)-propyl]-(7-benzyloxy-chroman-2-ylmethyl)amine;
(7-benzyloxy-chroman-2-ylmethyl)-(3-methoxy-propyl)amine;
3-[(2S)-7-benzyloxy-chroman-2-ylmethyl)-amino]-propan-1-ol;
3-{[(2R)-7-benzyloxy-chroman-2-ylmethyl]-amino}-propan-1-ol;
(7-benzyloxy-chroman-2-ylmethyl)-butyl-amine;
2-[(7-benzyloxy-chroman-2-ylmethyl)-amino]-ethanol;
(7-benzyloxy-chroman-2-ylmethyl)-(3-benzyloxy-propyl)-amine;
(7-benzyloxy-chroman-2-ylmethyl)-(3-phenyl-propyl)-amine;
(7-benzyloxy-chroman-2-ylmethyl)-(3-butoxy-propyl)-amine;
benzyl-(7-benzyloxy-chroman-2-ylmethyl)-amine;
3-{[7-(naphthalen-2-ylmethoxy)-chroman-2-ylmethyl]-amino}-propan-1-ol;

3-{[7-(4-nitro-benzyloxy)-chroman-2-ylmethyl]-amino}-propan-1-ol;
3-{[7-(2-chloro-benzyloxy)-chroman-2-ylmethyl]-amino}-propan-1-ol;
3-[(7-cyclohexylmethoxy-chroman-2-ylmethyl)-amino]-propan-1-ol;
3-{[7-(3-methoxy-benzyloxy)-chroman-2-ylmethyl]-amino}-propan-1-ol;
3-[(7-phenoxy-chroman-2-ylmethyl)-amino]-propan-1-ol;
(7-benzyloxy-chroman-2-yl)-methylamine;
2-[(7-benzyloxy-chroman-2-ylmethyl)-amino]-ethanol;
3-[(6-benzyloxy-benzofuran-2-ylmethyl)-amino]-propan-1-ol;
benzyl-(6-benzyloxy-benzofuran-2-ylmethyl)-amine;
3-[(7-benzyloxy-chroman-2-ylmethyl)-methyl-amino]-propan-1-ol;
(6-benzyloxy-2,3-dihydro-benzofuran-2-yl)-methylamine;
2-[(6-benzyloxy-2,3-dihydro-benzofuran-2-ylmethyl)-amino]-ethanol;
3-[(6-benzyloxy-2,3-dihydro-benzofuran-2-ylmethyl)-amino]-propan-1-ol;
[(2R)-7-benzyloxy-chroman-2-ylmethyl]-(3-methoxy-propyl)-amine;
[(2R)-7-benzyloxy-chroman-2-ylmethyl]-(3-ethoxy-propyl)-amine;
4-[(2R)-7-benzyloxy-chroman-2-ylmethyl]-morpholine;
benzyl-((2R)-7-benzyloxy-chroman-2-ylmethyl)-amine;
[(2R)-7-benzyloxy-chroman-2-ylmethyl]-(3-butoxy-propyl)-amine;
[(2R)-7-benzyloxy-chroman-2-ylmethyl]-tert-butyl-amine;
[(2R)-7-benzyloxy-chroman-2-ylmethyl]-(3-phenoxy-propyl)-amine;
3-[(7-benzyloxy-6-chloro-chroman-2-ylmethyl)-amino]-propan-1-ol;
1-(7-benzyloxy-chroman-2-ylmethyl)-4-(2-methoxy-phenyl)-piperazine;
7-{3-[(7-benzyloxy-6-chloro-chroman-2-ylmethyl)-amino]-propoxy}-chromen-2-one;
3-[(7-phenethyloxy-chroman-2-ylmethyl)-amino]-propan-1-ol;
3-{[7-(thiophen-3-ylmethoxy)-chroman-2-ylmethyl]-amino}-propan-1-ol;
(7-benzyloxy-chroman-2-ylmethyl)-[2-(1H-indol-3-yl)-ethyl]-amine;
3-[(7-benzyloxy-3-methyl-chroman-2-ylmethyl)-amino]-propan-1-ol;
3-{[7-(2-methyl-thiazol-4-ylmethoxy)-chroman-2-ylmethyl]-amino}-propan-1-ol;
7-{3-[(7-benzyloxy-chroman-2-ylmethyl)-amino]-propoxy}-chromen-2-one;
1-(7-benzyloxy-chroman-2-ylmethyl)-4-(2-methoxy-phenyl)-1,2,3,6-tetrahydropyridine;
3-[1-(7-benzyloxy-chroman-2-ylmethyl)-piperidin-4-yl]-1H-indole;
(7-benzyloxy-chroman-2-ylmethyl)-[3-(4-nitro-phenoxy)-propyl]-amine;
3-[(7-benzyloxy-3-butyl-chroman-2-ylmethyl)-amino]-propan-1-ol;
(7-benzyloxy-chroman-2-ylmethyl)-[3-(3-chloro-phenoxy)-propyl]-amine;
(7-benzyloxy-chroman-2-ylmethyl)-[3-(4-chloro-phenoxy)-propyl]-amine;
(7-benzyloxy-chroman-2-ylmethyl)-[3-(3-nitro-phenoxy)-propyl]-amine;
(7-benzyloxy-chroman-2-ylmethyl)-(2-benzylsulfanyl-ethyl)-amine;
(2R)-2-[(7-benzyloxy-chroman-2-ylmethyl)-amino]-3-benzylsulfanyl-propan-1-ol;
the stereoisomers thereof; or
the pharmaceutically acceptable salts thereof.

10. A method for the treatment of a disorder of the central nervous system related to or affected by the 5-HT6 receptor in a patient in need thereof which comprises providing said patient with a therapeutically effective amount of a compound of formula I

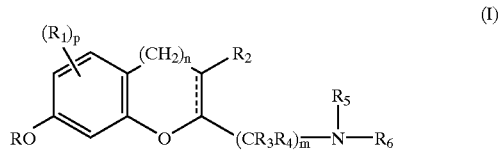

wherein
R is a substituted $C_1$–$C_6$alkyl group or an aryl or heteroaryl group each optionally substituted;
$R_1$ is halogen, CN, $OR_7$, $CO_2R_8$, $CONR_9R_{10}$, $SO_xR_{11}$ or a $C_1$–$C_6$alkyl, $C_2$–$C_6$alkenyl, $C_2$–$C_6$alkynyl, $C_3$–$C_6$cycloalkyl, cycloheteroalkyl, phenyl or heteroaryl group each optionally substituted;
$R_2$ $R_3$ and $R_4$ are each independently H or an optionally substituted $C_1$–$C_6$ alkyl group with the proviso that when R is a substituted $C_1$–$C_6$alkyl group then $R_2$ $R_3$ and $R_4$ must be H;
$R_5$ and $R_6$ are each independently H or a $C_1$–$C_6$alkyl, $C_3$–$C_6$cycloalkyl or heterocyclylalkyl group each optionally substituted or $R_5$ and $R_6$ may be taken together with the atom to which they are attached to represent a 3- to 10-membered optionally substituted mono- or bicyclic ring system optionally containing one or two additional heteroatoms selected from N, O or S with the proviso that when R is a substituted $C_1$–$C_6$alkyl group then $R_5$ and $R_6$ must be other than a $C_3$–$C_6$cycloalkyl or cycloheteroalkyl group;
m is an integer of 1, 2, 3 or 4;
n is 0 or 1;
p is 0 or an integer of 1, 2 or 3;
=== represents a single bond or a double bond;
x is 0 or an integer of 1 or 2;
$R_7$ is H, $CO_2R_{12}$ or a $C_1$–$C_6$alkyl, $C_2$–$C_6$alkenyl, $C_2$–$C_6$alkynyl, aryl or heteroaryl group each optionally substituted;
$R_8$ and $R_{12}$ are each independently H or a $C_1$–$C_6$alkyl, $C_2$–$C_6$alkenyl, $C_2$–$C_6$alkynyl, $C_3$–$C_6$cycloalkyl, cycloheteroalkyl, aryl or heteroaryl group each optionally substituted;
$R_9$ and $R_{10}$ are each independently H or an optionally substituted $C_1$–$C_6$alkyl group; and
$R_{11}$ is a $C_1$–$C_6$alkyl, aryl or heteroaryl group each optionally substituted; or
the stereoisomers thereof or a pharmaceutically acceptable salt thereof.

11. The method according to claim 10 wherein said disorder is a motor disorder, anxiety disorder or cognitive disorder.

12. The method according to claim 10 wherein said disorder is schizophrenia or depression.

13. The method according to claim 11 wherein said disorder is Alzheimer's disease or Parkinson's disease.

14. The method according to claim 11 wherein said disorder is attention deficit disorder or obsessive compulsive disorder.

15. A pharmaceutical composition which comprises a pharmaceutically acceptable carrier and an effective amount of a compound of formula I

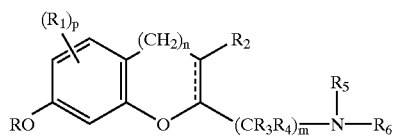

(I)

wherein
R is a substituted $C_1$–$C_6$alkyl group, or an aryl or heteroaryl group each optionally substituted;
$R_1$ is halogen, CN, $OR_7$, $CO_2R_8$, $CONR_9R_{10}$, $SO_xR_{11}$ or a $C_1$–$C_6$alkyl, $C_2$–$C_6$alkenyl, $C_2$–$C_6$alkynyl, $C_3$–$C_6$cycloalkyl, cycloheteroalkyl, phenyl or heteroaryl group each optionally substituted;
$R_2$, $R_3$ and $R_4$ are each independently H or an optionally substituted $C_1$–$C_6$ alkyl group with the proviso that when R is a substituted $C_1$–$C_6$alkyl group then $R_2$, $R_3$ and $R_4$ must be H;
$R_5$ and $R_6$ are each independently H or a $C_1$–$C_6$alkyl, $C_3$–$C_6$cycloalkyl or heterocyclylalkyl group each optionally substituted or $R_5$ and $R_6$ may be taken together with the atom to which they are attached to represent a 3- to 10-membered optionally substituted mono- or bicyclic ring system optionally containing one or two additional heteroatoms selected from N, O or S with the proviso that when R is a substituted $C_1$–$C_6$alkyl group then $R_5$ and $R_6$ must be other than a $C_3$–$C_6$cycloalkyl or cycloheteroalkyl group;
m is an integer of 1, 2, 3 or 4;
n is 0 or 1;
p is 0 or an integer of 1, 2 or 3;
=== represents a single bond or a double bond;
x is 0 or an integer of 1 or 2;
$R_7$ is H, $CO_2R_{12}$ or a $C_1$–$C_6$alkyl, $C_2$–$C_6$alkenyl, $C_2$–$C_6$alkynyl, aryl or heteroaryl group each optionally substituted;
$R_8$ and $R_{12}$ are each independently H or a $C_1$–$C_6$alkyl, $C_2$–$C_6$alkenyl, $C_2$–$C_6$alkynyl, $C_3$–$C_6$cycloalkyl, cycloheteroalkyl, aryl or heteroaryl group each optionally substituted;
$R_9$ and $R_{10}$ are each independently H or an optionally substituted $C_1$–$C_6$alkyl group; and
$R_{11}$ is a $C_1$–$C_6$alkyl, aryl or heteroaryl group each optionally substituted; or
the stereoisomers thereof or a pharmaceutically acceptable salt thereof.

16. The composition according to claim 15 having a formula I compound wherein R is a substituted $C_1$–$C_6$alkyl group.

17. The composition according to claim 16 having a formula I compound wherein === represents a single bond; m is 1; and $R_5$ and $R_6$ are each independently H or an optionally substituted $C_1$–$C_6$alkyl group.

18. The composition according to claim 17 having a formula I compound wherein n is 1; p is 0 or 1; and $R_2$ is H.

19. The composition according to claim 17 having a formula I compound selected from the group consisting of:
[3-(benzoxazol-6-yloxy)-propyl]-(7-benzyloxy-chroman-2-ylmethyl)amine;
(7-benzyloxy-chroman-2-ylmethyl)-(3-methoxy-propyl)amine;
3-[(2S)-7-benzyloxy-chroman-2-ylmethyl)-amino]-propan-1-ol;
3-{[(2R)-7-benzyloxy-chroman-2-ylmethyl]-amino}-propan-1-ol;
(7-benzyloxy-chroman-2-ylmethyl)-butyl-amine;
2-[(7-benzyloxy-chroman-2-ylmethyl)-amino]-ethanol;
(7-benzyloxy-chroman-2-ylmethyl)-(3-benzyloxy-propyl)-amine;
(7-benzyloxy-chroman-2-ylmethyl)-(3-phenyl-propyl)-amine;
(7-benzyloxy-chroman-2-ylmethyl)-(3-butoxy-propyl)-amine;
benzyl-(7-benzyloxy-chroman-2-ylmethyl)-amine;
3-{[7-(naphthalen-2-ylmethoxy)-chroman-2-ylmethyl]-amino}-propan-1-ol;
3-{[7-(4-nitro-benzyloxy)-chroman-2-ylmethyl]-amino}-propan-1-ol;
3-{[7-(2-chloro-benzyloxy)-chroman-2-ylmethyl]-amino}-propan-1-ol;
3-[(7-cyclohexylmethoxy-chroman-2-ylmethyl)-amino]-propan-1-ol;
3-{[(7-(3-methoxy-benzyloxy)-chroman-2-ylmethyl]-amino}-propan-1-ol;
3-[(7-phenoxy-chroman-2-ylmethyl)-amino]-propan-1-ol;
(7-benzyloxy-chroman-2-yl)-methylamine;
2-[(7-benzyloxy-chroman-2-ylmethyl)-amino]-ethanol;
3-[(6-benzyloxy-benzofuran-2-ylmethyl)-amino]-propan-1-ol;
benzyl-(6-benzyloxy-benzofuran-2-ylmethyl)-amine;
3-[(7-benzyloxy-chroman-2-ylmethyl)-methyl-amino]-propan-1-ol;
(6-benzyloxy-2,3-dihydro-benzofuran-2-yl)-methylamine;
2-[(6-benzyloxy-2,3-dihydro-benzofuran-2-ylmethyl)-amino]-ethanol;
3-[(6-benzyloxy-2,3-dihydro-benzofuran-2-ylmethyl)-amino]-propan-1-ol;
[(2R)-7-benzyloxy-chroman-2-ylmethyl]-(3-methoxy-propyl)-amine;
[(2R)-7-benzyloxy-chroman-2-ylmethyl]-(3-ethoxy-propyl)-amine;
4-[(2R)-7-benzyloxy-chroman-2-ylmethyl]-morpholine;
benzyl-((2R)-7-benzyloxy-chroman-2-ylmethyl)-amine;
[(2R)-7-benzyloxy-chroman-2-ylmethyl]-(3-butoxy-propyl)-amine;
[(2R)-7-benzyloxy-chroman-2-ylmethyl]-tert-butyl-amine;
[(2R)-7-benzyloxy-chroman-2-ylmethyl]-(3-phenoxy-propyl)-amine;
3-[(7-benzyloxy-6-chloro-chroman-2-ylmethyl)-amino]-propan-1-ol;

1-(7-benzyloxy-chroman-2-ylmethyl)-4-(2-methoxy-phenyl)-piperazine;
7-{3-[(7-benzyloxy-6-chloro-chroman-2-ylmethyl)-amino]-propoxy}-chromen-2-one;
3-[(7-phenethyloxy-chroman-2-ylmethyl)-amino]-propan-1-ol;
3-{[7-(thiophen-3-ylmethoxy)-chroman-2-ylmethyl]-amino}-propan-1-ol;
(7-benzyloxy-chroman-2-ylmethyl)-[2-(1H-indol-3-yl)-ethyl]-amine;
3-[(7-benzyloxy-3-methyl-chroman-2-ylmethyl)-amino]-propan-1-ol;
3-{[7-(2-methyl-thiazol-4-ylmethoxy)-chroman-2-ylmethyl]-amino}-propan-1-ol;
7-{3-[(7-benzyloxy-chroman-2-ylmethyl)-amino]-propoxy}-chromen-2-one;
1-(7-benzyloxy-chroman-2-ylmethyl)-4-(2-methoxy-phenyl)-1,2,3,6-tetrahydropyridine;
3-[1-(7-benzyloxy-chroman-2-ylmethyl)-piperidin-4-yl]-1H-indole;
(7-benzyloxy-chroman-2-ylmethyl)-[3-(4-nitro-phenoxy)-propyl]-amine;
3-[(7-benzyloxy-3-butyl-chroman-2-ylmethyl)-amino]-propan-1-ol;
(7-benzyloxy-chroman-2-ylmethyl)-[3-(3-chloro-phenoxy)-propyl]-amine;
(7-benzyloxy-chroman-2-ylmethyl)-[3-(4-chloro-phenoxy)-propyl]-amine;
(7-benzyloxy-chroman-2-ylmethyl)-[3-(3-nitro-phenoxy)-propyl]-amine;
(7-benzyloxy-chroman-2-ylmethyl)-(2-benzylsulfanyl-ethyl)-amine;
(2R)-2-[(7-benzyloxy-chroman-2-ylmethyl)-amino]-3-benzylsulfanyl-propan-1-ol;

the stereoisomers thereof; or
the pharmaceutically acceptable salts thereof.

20. A process for the preparation of a compound of formula I

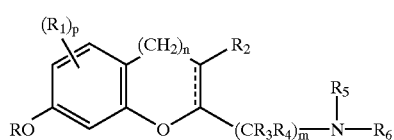

(I)

wherein
R is a substituted $C_1$–$C_6$alkyl group, or an aryl or heteroaryl group each optionally substituted;
$R_1$ is halogen, CN, $OR_7$, $CO_2R_8$, $CONR_9R_{10}$, $SO_xR_{11}$ or a $C_1$–$C_6$alkyl, $C_2$–$C_6$alkenyl, $C_2$–$C_6$alkynyl, $C_3$–$C_6$cycloalkyl, cycloheteroalkyl, phenyl or heteroaryl group each optionally substituted;
$R_2$, $R_3$ and $R_4$ are each independently H or an optionally substituted $C_1$–$C_6$ alkyl group with the proviso that when R is a substituted $C_1$–$C_6$alkyl group then $R_2$, $R_3$ and $R_4$ must be H;
$R_5$ and $R_6$ are each independently H or a $C_1$–$C_6$alkyl, $C_3$–$C_6$cycloalkyl or heterocyclylalkyl group each optionally substituted or $R_5$ and $R_6$ may be taken together with the atom to which they are attached to represent a 3- to 10-membered optionally substituted mono- or bicyclic ring system optionally containing one or two additional heteroatoms selected from N, O or S with the proviso that when R is a substituted $C_1$–$C_6$alkyl group then $R_5$ and $R_6$ must be other than a $C_3$–$C_6$cycloalkyl or cycloheteroalkyl group;
m is an integer of 1, 2, 3 or 4;
n is 0 or 1;
p is 0 or an integer of 1, 2 or 3;
=== represents a single bond or a double bond;
x is 0 or an integer of 1 or 2;
$R_7$ is H, $CO_2R_{12}$ or a $C_1$–$C_6$alkyl, $C_2$–$C_6$alkenyl, $C_2$–$C_6$alkynyl, aryl or heteroaryl group each optionally substituted;
$R_8$ and $R_{12}$ are each independently H or a $C_1$–$C_6$alkyl, $C_2$–$C_6$alkenyl, $C_2$–$C_6$alkynyl, $C_3$–$C_6$cycloalkyl, cycloheteroalkyl, aryl or heteroaryl group each optionally substituted;
$R_9$ and $R_{10}$ are each independently H or an optionally substituted $C_1$–$C_6$alkyl group; and
$R_{11}$ is a $C_1$–$C_6$alkyl, aryl or heteroaryl group each optionally substituted which process comprises reacting a compound of formula II

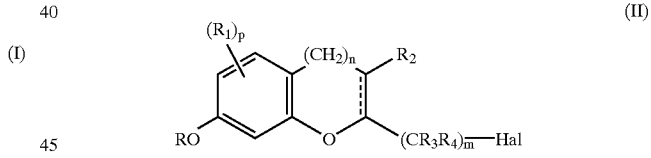

(II)

wherein R, $R_1$, $R_2$, $R_3$, $R_4$, m, n and p are as defined hereinabove and Hal represents Cl or Br with an amine, $HNR_5R_6$, at an elevated temperature optionally in the presence of a solvent to give the desired product of formula I.

* * * * *